US012584918B2

(12) United States Patent
Anderson et al.

(10) Patent No.: US 12,584,918 B2
(45) Date of Patent: Mar. 24, 2026

(54) MULTIPLEXED LATERAL FLOW ASSAY FOR DETECTION OF HPV ASSOCIATED CANCER

(71) Applicants: Karen Anderson, Scottsdale, AZ (US); Ching-Wen Hou, Chandler, AZ (US)

(72) Inventors: Karen Anderson, Scottsdale, AZ (US); Ching-Wen Hou, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 799 days.

(21) Appl. No.: 17/950,308

(22) Filed: Sep. 22, 2022

(65) Prior Publication Data

US 2023/0105995 A1 Apr. 6, 2023

Related U.S. Application Data

(60) Provisional application No. 63/247,759, filed on Sep. 23, 2021.

(51) Int. Cl.
| | |
|---|---|
| *G01N 33/569* | (2006.01) |
| *G01N 33/574* | (2006.01) |
| *G01N 33/58* | (2006.01) |

(52) U.S. Cl.
CPC .................. *G01N 33/56983* (2013.01); *G01N 33/57407* (2013.01); *G01N 33/582* (2013.01); *G01N 2333/025* (2013.01); *G01N 2469/20* (2013.01)

(58) Field of Classification Search
CPC ....... G01N 33/56983; G01N 33/57407; G01N 33/582; G01N 2333/025; G01N 2469/20
See application file for complete search history.

(56) References Cited

U.S. PATENT DOCUMENTS

| | | | |
|---|---|---|---|
| 7,396,664 B2 | 7/2008 | Daly et al. | |
| 2007/0053922 A1* | 3/2007 | Sette ....................... | A61P 31/20 |
| | | | 530/350 |
| 2018/0172681 A1* | 6/2018 | Katchman ........ | G01N 33/54386 |

OTHER PUBLICATIONS

Liu Y, Cherry JJ, Dineen JV, Androphy EJ, Baleja JD. Determinants of Stability for the E6 Protein of Papillomavirus Type 16. J Mol Bio; vol. 386, Iss. 4, 2009: pp. 1123-1137. (Year: 2009).*
Verma RR, Sriraman R, et al. E6 protein of human papillomavirus 16 (HPV16) expressed in *Escherichia coli* sans a stretch of hydrophobic amino acids, enables purification of GST-ΔE6 in the soluble form and retains the binding ability to p53. Protein Expr Purif. Nov. 2013;92(1):41-7. Epub Sep. 6, 2013. (Year: 2013).*
Anderson KS, Gerber JE, D'Souza G, Pai SI, Cheng JN, Alam R, Kesiraju S, Chowell D, Gross ND, Haddad R, Gillison ML, Posner M. Biologic predictors of serologic responses to HPV in oropharyngeal cancer: The HOTSPOT study. Oral Oncol. 2015;51(8):751-8. Epub Jun. 23, 2015. doi: 10.1016/j.oraloncology.2015.05.007. PubMed PMID: 26094591; PMCID: PMC4982366.
Baumann R, Kaempfer S, Chegou NN, Oehlmann W, Loxton AG, Kaufmann SH, van Helden PD, Black GF, Singh M, Walzl G. Serologic diagnosis of tuberculosis by combining Ig classes against selected mycobacterial targets. J Infect. 2014;69(6):581-9. Epub Jun. 27, 2014. doi:10.1016/j.jinf.2014.05.014. PubMed PMID: 24968240.
Burbelo PD, Chaturvedi A, Notkins AL, Gunti S. Luciferase-Based Detection of Antibodies for the Diagnosis of HPV-Associated Head and Neck Squamous Cell Carcinoma. Diagnostics (Basel). 2019;9(3). Epub Aug. 9, 2019. doi: 10.3390/diagnostics9030089. PubMed PMID: 31390810; PMCID: PMC6787723.
Chaturvedi AK, Engels EA, Pfeiffer RM, Hernandez BY, Xiao W, Kim E, Jiang B, Goodman MT, Sibug-Saber M, Cozen W, Liu L, Lynch CF, Wentzensen N, Jordan RC, Altekruse S, Anderson WF, Rosenberg PS, Gillison ML. Human papillomavirus and rising oropharyngeal cancer incidence in the United States. J Clin Oncol. 2011;29(32):4294-301. Epub Oct. 5, 2011. doi: 10.1200/JCO.2011.36.4596. PubMed PMID: 21969503; PMCID: PMC3221528.
Chen ZW, Weinreb I, Kamel-Reid S, Perez-Ordonez B. Equivocal p16 immunostaining in squamous cell carcinoma of the head and neck: staining patterns are suggestive of HPV status. Head Neck Pathol. 2012;6(4):422-9. Epub Jul. 18, 2012. doi: 10.1007/s12105-012-0382-3. PubMed PMID: 22801997; PMCID: PMC3500888.
Chow LQM. Head and Neck Cancer. N Engl J Med. 2020;382(1):60-72. Epub 2020/01/02. doi: 10.1056/NEJMra1715715. PubMed PMID: 31893516.
Corstjens PL, Abrams WR, Malamud D. Detecting viruses by using salivary diagnostics. J Am Dent Assoc. 2012; 143(10 Suppl):12S-8S. Epub Oct. 17, 2012. doi: 10.14219/jada.archive.2012.0338. PubMed PMID: 23034833; PMCID: PMC4262792.
Dahlstrom KR, Anderson KS, Field MS, Chowell D, Ning J, Li N, Wei Q, Li G, Sturgis EM. Diagnostic accuracy of serum antibodies to human papillomavirus type 16 early antigens in the detection of human papillomavirus-related oropharyngeal cancer. Cancer. 2017;123(24):4886-94. Epub Sep. 13, 2017. doi: 10.1002/cncr.30955. PubMed PMID: 28898394; PMCID: PMC5716885.
D'Souza G, Clemens G, Troy T, Castillo RG, Struijk L, Waterboer T, Bender N, Pierorazio PM, Best SR, Strickler H, Wiley DJ, Haddad RI, Posner M, Fakhry C. Evaluating the Utility and Prevalence of HPV Biomarkers in Oral Rinses and Serology for HPV-related Oropharyngeal Cancer. Cancer Prev Res (Phila). 2019;12(10):689-700. Epub Aug. 20, 2019. doi: 10.1158/1940-6207.CAPR-19-0185. PubMed PMID: 31420362; PMCID: PMC7029397.

(Continued)

*Primary Examiner* — Rachel B Gill
(74) *Attorney, Agent, or Firm* — Quarles & Brady, LLP

(57) ABSTRACT

Methods and compositions are provided for the detection of HPV infection in a subject sample. In particular, the methods and composition include variants of certain HPV proteins (e.g., HPV16 E6 protein), wherein the HPV proteins have been modified to enhance solubility while maintaining or enhancing seropositivity to HPV positive plasma/sera. Additional methods and compositions relate to improving purification of HPV proteins through the use of modified amino acid sequences. These approaches may enhance the performance of serological detection techniques and support broader implementation of detection assays.

15 Claims, 14 Drawing Sheets

Specification includes a Sequence Listing.

(56)        References Cited

OTHER PUBLICATIONS

D'Souza G, Gross ND, Pai SI, Haddad R, Anderson KS, Rajan S, Gerber J, Gillison ML, Posner MR. Oral human papillomavirus (HPV) infection in HPV-positive patients with oropharyngeal cancer and their partners. J Clin Oncol. 2014;32(23):2408-15. Epub Apr. 30, 2014. doi: 10.1200/JCO.2014.55.1341. PubMed PMID: 24778397; PMCID: PMC4263818.

Ellington AA, Kullo IJ, Bailey KR, Klee GG. Antibody-based protein multiplex platforms: technical and operational challenges. Clin Chem. 2010;56(2):186-93. Epub Dec. 5, 2009. doi: 10.1373/clinchem.2009.127514. PubMed PMID: 19959625; PMCID:PMC2901849.

Evander M, Edlund K, Gustafsson A, Jonsson M, Karlsson R, Rylander E, Wadell G. Human papillomavirus infection is transient in young women: a population-based cohort study. J Infect Dis. 1995;171(4):1026-30. Epub Apr. 1, 1995. doi: 10.1093/infdis/171. 4.1026. PubMed PMID: 7706782.

Fakhry C, Qualliotine JR, Zhang Z, Agrawal N, Gaykalova DA, Bishop JA, Subramaniam RM, Koch WM, Chung CH, Eisele DW, Califano J, Viscidi RP. Serum Antibodies to HPV16 Early Proteins Warrant Investigation as Potential Biomarkers for Risk Stratification and Recurrence of HPV-Associated Oropharyngeal Cancer. Cancer Prev Res (Phila). 2016;9(2):135-41. Epub Dec. 25, 2015. doi: 10.1158/1940-6207.CAPR-15-0299. PubMed PMID: 26701665; PMCID: PMC4811031.

Guo WZFMQS. Gynecologic and Obstetric Pathology, vol. 2: Springer, Singapore;2019.

Holzinger D, Wichmann G, Baboci L, Michel A, Hofler D, Wiesenfarth M, Schroeder L, Boscolo-Rizzo P, Herold-Mende C, Dyckhoff G, Boehm A, Del Mistro A, Bosch FX, Dietz A, Pawlita M, Waterboer T. Sensitivity and specificity of antibodies against HPV16 E6 and other early proteins for the detection of HPV16-driven oropharyngeal squamous cell carcinoma. Int J Cancer. 2017;140(12):2748-57. Epub Mar. 21, 2017. doi: 10.1002/ijc.30697. PubMed PMID:28316084.

Hou C, Zhu M, Anderson KS, Obahiagbon U, Christen JB, editors. Assay Development and Storage for Fluorescence-Based Lateral Flow Immunoassay. 2018 IEEE Life Sciences Conference (LSC); 2018 Oct. 28-30, 2018.

Hsing AW, Schiffman M, Zhang T, Greer CE, Chen CJ, You SL, Hsieh CY, Huang TW, Liaw KL, Manos M. Persistence of type-specific human papillomavirus infection among cytologically normal women. J Infect Dis. 1994;170(2):498. Epub Aug. 1, 1994. doi: 10.1093/infdis/170.2.498. PubMed PMID: 8035046.

Illiano E, Demurtas OC, Massa S, Di Bonito P, Consalvi V, Chiaraluce R, Zanotto C, De Giuli Morghen C, Radaelli A, Venuti A, Franconi R. Production of functional, stable, unmutated recombinant human papillomavirus E6 oncoprotein: implications for HPV-tumor diagnosis and therapy. J Transl Med. 2016;14(1):224. Epub Jul. 29, 2016. doi: 10.1186/s12967-016-0978-6. PubMed PMID: 27465494; PMCID: PMC4963926.

Inan H, Wang S, Inci F, Baday M, Zangar R, Kesiraju S, Anderson KS, Cunningham BT, Demirci U. Isolation, Detection, and Quantification of Cancer Biomarkers in HPV-Associated Malignancies. Sci Rep. 2017;7(1):3322. Epub Jun. 14, 2017. doi: 10.1038/s41598-017-02672-6. PubMed PMID: 28607383; PMCID: PMC5468352.

Katchman BA, Smith JT, Obahiagbon U, Kesiraju S, Lee YK, O'Brien B, Kaftanoglu K, Blain Christen J, Anderson KS. Application of flat panel OLED display technology for the pointof-care detection of circulating cancer biomarkers. Sci Rep. 2016;6:29057. Epub Jul. 5, 2016. doi: 10.1038/srep29057. PubMed PMID: 27374875; PMCID: PMC4931450.

Kim KY, Lewis JS, Jr., Chen Z. Current status of clinical testing for human papillomavirus in oropharyngeal squamous cell carcinoma. J Pathol Clin Res. 2018;4(4):213-26. Epub Jul. 31, 2018. doi: 10.1002/cjp2.111. PubMed PMID: 30058293; PMCID: PMC6174616.

Kreimer AR, Clifford GM, Boyle P, Franceschi S. Human papillomavirus types in head and neck squamous cell carcinomas worldwide: a systematic review. Cancer Epidemiol Biomarkers Prev.

2005;14(2):467-75. Epub Mar. 1, 2005. doi: 10.1158/1055-9965. EPI-04-0551. PubMed PMID: 15734974.

Kreimer et al., Timing of HPV16-E6 antibody seroconversion before OPSCC: findings from the HPVC3 consortium. Ann Oncol. 2019;30(8):1335-43. Epub Jun. 12, 2019. doi: 10.1093/annonc/mdz138. PubMed PMID:31185496; PMCID: PMC6683856.

Kreimer et al., Evaluation of human papillomavirus antibodies and risk of subsequent head and neck cancer. J Clin Oncol. 2013;31(21):2708-15. Epub Jun. 19, 2013. doi: 10.1200/JCO.2012. 47.2738. PubMed PMID: 23775966; PMCID: PMC3709056.

Kubik MJ, Permenter T, Saremian J. Specimen Age Stability for Human Papilloma Virus DNA Testing Using BD SurePath. Lab Med. 2015;46(1):51-4; quiz e13. Epub Jan. 27, 2015. doi: 10.1309/LM87NED5LRSELUOQ. PubMed PMID: 25617393.

Kumar P, et al., (2021) AOGIN conference.

Landy, A. (1989) Dynamic, Structural, and Regulatory Aspects of Lambda Site-specific Recombination. Ann. Rev. Biochem. 58, 913-949.

Marur S, D'Souza G, Westra WH, Forastiere AA. HPV-associated head and neck cancer: a virus-related cancer epidemic. Lancet Oncol. 2010;11(8):781-9. Epub May 11, 2010. doi: 10.1016/S1470-2045(10)70017-6. PubMed PMID: 20451455; PMCID: PMC5242182.

Millipore M. Microsphere Coupling—Two-step EDC/Sulfo NHS Covalent Coupling Procedure for Estapor Carboxyl-modified Dyed Microspheres 2015.

Morbini P, Benazzo M. Human papillomavirus and head and neck carcinomas: focus on evidence in the babel of published data. Acta Otorhinolaryngol Ital. 2016;36(4):249-58. Epub Oct. 14, 2016. doi: 10.14639/0392-100X-853. PubMed PMID: 27734976; PMCID: PMC5066459.

Moscicki AB, Palefsky J, Smith G, Siboshski S, Schoolnik G. Variability of human papillomavirus DNA testing in a longitudinal cohort of young women. Obstet Gynecol. 1993;82(4 Pt 1):578-85. Epub Oct. 1, 1993. PubMed PMID: 8397358.

Obahiagbon U, Smith JT, Zhu M, Katchman BA, Arafa H, Anderson KS, Blain Christen Jm. A compact, low-cost, quantitative and multiplexed fluorescence detection platform for pointof-care applications. Biosens Bioelectron. 2018;117:153-60. Epub Jun. 13, 2018. doi: 10.1016/j.bios.2018.04.002. PubMed PMID: 29894852; PMCID: PMC6095205.

Pierce Campbell CM, Kreimer AR, Lin HY, Fulp W, O'Keefe MT, Ingles DJ, Abrahamsen M, Villa LL, Lazcano-Ponce E, Giuliano AR. Long-term persistence of oral human papillomavirus type 16: the HPV Infection in Men (HIM) study. Cancer Prev Res (Phila). 2015;8(3):190-6. Epub Jan. 13, 2015. doi: 10.1158/1940-6207. CAPR-14-0296. PubMed PMID: 25575501; PMCID: PMC4355174.

Rosenberg, A. H., Lade, B. N., Chui, D.-S., Lin, S.-W., Dunn, J. J., and Studier, F. W. (1987) Vectors for Selective Expression of Cloned DNAs by T7 RNA Polymerase. Gene 56, 125-135.

Siegel RL, Miller KD, Jemal A. Cancer statistics, 2020. CA Cancer J Clin. 2020;70(1):7-30. Epub Jan. 9, 2020. doi: 10.3322/caac. 21590. PubMed PMID: 31912902.

Silverberg MJ, Schneider MF, Silver B, Anastos KM, Burk RD, Minkoff H, Palefsky J, Levine AM, Viscidi RP. Serological detection of human papillomavirus type 16 infection in human immunodeficiency virus (HIV)-positive and high-risk HIV-negative women. Clin Vaccine Immunol. 2006;13(4):511-9. Epub Apr. 11, 2006. doi: 10.1128/CVI.13.4.511-519.2006. PubMed PMID: 16603621; PMCID: PMC1459636.

Spector ME, Sacco AG, Bellile E, Taylor JMG, Jones T, Sun K, Brown WC, Birkeland AC, Bradford CR, Wolf GT, Prince ME, Moyer JS, Malloy K, Swiecicki P, Eisbruch A, McHugh JB, Chepeha DB, Rozek L, Worden FP. E6 and E7 Antibody Levels Are Potential Biomarkers of Recurrence in Patients with Advanced-Stage Human Papillomavirus-Positive Oropharyngeal Squamous Cell Carcinoma. Clin Cancer Res. 2017;23(11):2723-9. Epub Nov. 23, 2016. doi: 10.1158/1078-0432.CCR-16-1617. PubMed PMID: 27872102; PMCID: PMC5438906.

Studier, F. W., and Moffatt, B. A. (1986) Use of Bacteriophage T7 RNA Polymerase to Direct Selective High-Level Expression of Cloned Genes. J. Mol. Biol. 189, 113-130.

(56) References Cited

OTHER PUBLICATIONS

Studier, F. W., Rosenberg, A. H., Dunn, J. J., and Dubendorff, J. W. (1990) Use of T7 RNA Polymerase to Direct Expression of Cloned Genes. Meth. Enzymol. 185, 60-89.

Taberna M, Mena M, Pavon MA, Alemany L, Gillison ML, Mesia R. Human papillomavirus-related oropharyngeal cancer. Ann Oncol. 2017;28(10):2386-98. Epub Jun. 22, 2017. doi: 10.1093/annonc/mdx304. PubMed PMID: 28633362.

Tang KD, Vasani S, Taheri T, Walsh LJ, Hughes BGM, Kenny L, Punyadeera C. An Occult HPV-Driven Oropharyngeal Squamous Cell Carcinoma Discovered Through a Saliva Test. Front Oncol. 2020;10:408. Epub Apr. 17, 2020. doi: 10.3389/fonc.2020.00408. PubMed PMID: 32296641; PMCID: PMC7136454.

Thomas GR, Jefferson G. Chapter 64—Head and Neck Cancer. In: Ginsburg GS, Willard HF, editors. Genomic and Personalized Medicine (Second Edition): Academic Press; 2013. p. 742-8.

Verma RR, Sriraman R, Rana SK, Ponnanna NM, Rajendar B, Ghantasala p. Rajendra L, Matur RV, Srinivasan VA. E6 protein of human papillomavirus 16 (HPV16) expressed in *Escherichia coli* sans a stretch of hydrophobic amino acids, enables purification of GST-DeltaE6 in the soluble form and retains the binding ability to p53. Protein Expr Purif. 2013;92(1):41-7. Epub Sep. 10, 2013. doi: 10.1016/j.pep.2013.08.010. PubMed PMID: 24012792.

Won KH, Lee JY, Cho HY, Suh DH, No. JH, Kim YB. Impact of age on the false negative rate of human papillomavirus DNA test in patients with atypical squamous cells of undetermined significance. Obstet Gynecol Sci. 2015;58(2):117-23. Epub Maar. 24, 2015. doi: 10.5468/ogs.2015.58.2.117. PubMed PMID: 25798425; PMCID: PMC4366864.

Wu MZ, Li WN, Cha N, Tian LX, Zhang YI, Wu X, Guo KJ, Wu GP. Diagnostic Utility of HPV16 E6 mRNA or E7 mRNA Quantitative Expression for Cervical Cells of Patients with Dysplasia and Carcinoma. Cell Transplant. 2018;27(9):1401-6. Epub Jul. 31, 2018. doi: 10.1177/0963689718788521. PubMed PMID: 30056761; PMCID: PMC6168995.

Xu WX, Wang J, Tang HP, He YP, Zhu QX, Gupta SK, Gu SH, Huang Q, Ji CN, Liu LF, Li GL, Xu CJ, Xie Y. Epitomics: IgG-epitome decoding of E6, E7 and L1 proteins from oncogenic human papillomavirus type 58. Sci Rep. 2016;6:34686. Epub Oct. 7, 2016. doi: 10.1038/srep34686. PubMed PMID: 27708433; PMCID: PMC5052575.

* cited by examiner

Photodiode

Emission filter

Nitrocellulose membrane

Excitation filter

LED

HPV16 NE6

| Sample CV (%) | 1 | 2 | 3 | 4 | 5 | 6 |
|---|---|---|---|---|---|---|
| Batch 1 (Intra) | 3.17% | 9.56% | 11.96% | 12.59% | 29.46% | 8.53% |
| Batch 2 (Intra) | 5.82% | 4.86% | 13.32% | 18.37% | 12.83% | 10.76% |
| Total (Inter) | 11.27% | 13.81% | 12.15% | 14.61% | 26.93% | 9.98% |

HPV16 CE2

| Sample CV (%) | 1 | 2 | 3 | 4 | 5 | 6 |
|---|---|---|---|---|---|---|
| Batch 1 (Intra) | 5.82% | 17.92% | 15.84% | 15.70% | 24.81% | 1.46% |
| Batch 2 (Intra) | 8.93% | 12.3% | 16.65% | 1.64% | 13.96% | 13.53% |
| Total (Inter) | 13.23% | 18.35% | 20.77% | 11.23% | 16.88% | 17.43% |

HPV16 E7

| Sample CV (%) | 1 | 2 | 3 | 4 | 5 | 6 |
|---|---|---|---|---|---|---|
| Batch 1 (Intra) | 6.56% | 22.24% | 10.61% | 18.09% | 21.76% | 12.75% |
| Batch 2 (Intra) | 5.09% | 13.34% | 8.86% | 8.86% | 29.38% | 20.76% |
| Total (Inter) | 14.56% | 18.08% | 12.90% | 14.84% | 23.18% | 18.64% |

FIGURE 10A

Figure 10B:
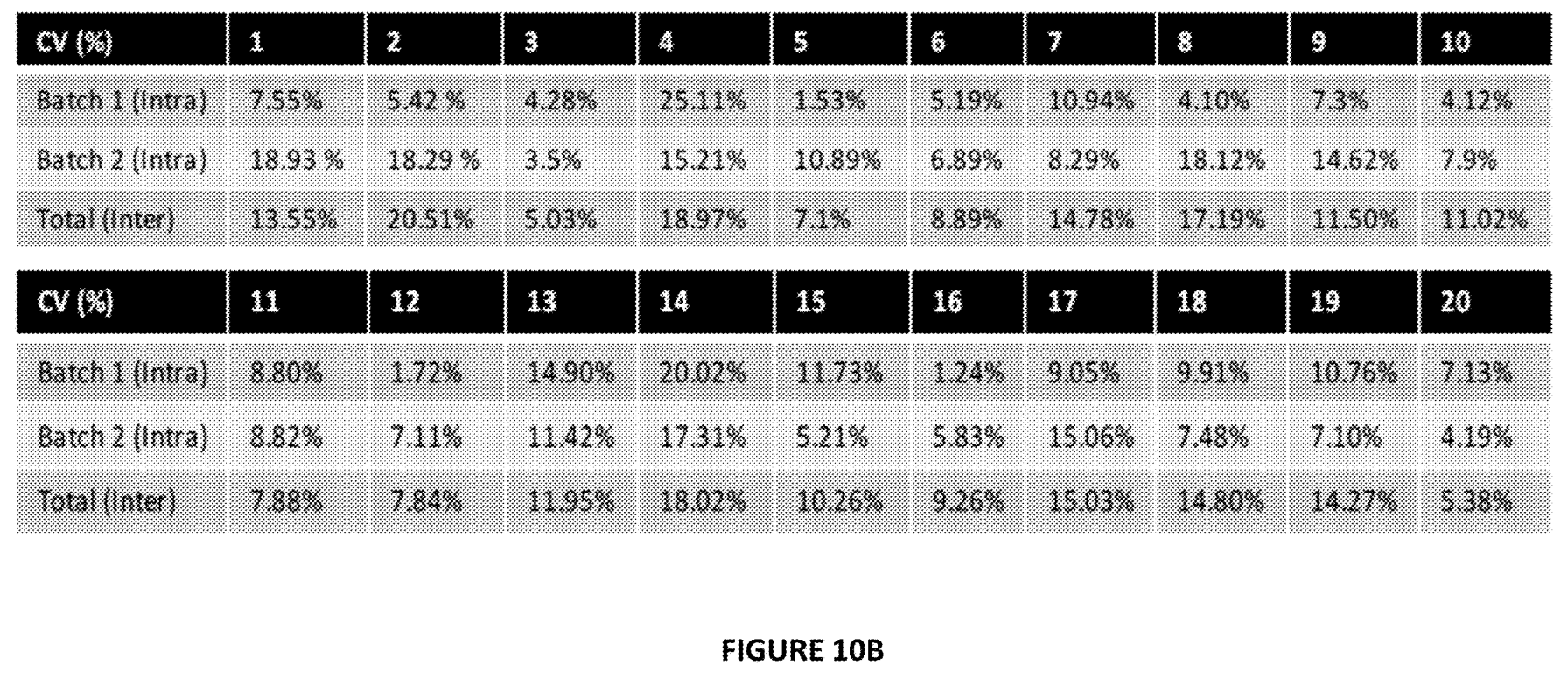

| CV (%) | 1 | 2 | 3 | 4 | 5 | 6 | 7 | 8 | 9 | 10 |
|---|---|---|---|---|---|---|---|---|---|---|
| Batch 1 (Intra) | 7.55% | 5.42 % | 4.28% | 25.11% | 1.53% | 5.19% | 10.94% | 4.10% | 7.3% | 4.12% |
| Batch 2 (Intra) | 18.93 % | 18.29 % | 3.5% | 15.21% | 10.89% | 6.89% | 8.29% | 18.12% | 14.62% | 7.9% |
| Total (Inter) | 13.55% | 20.51% | 5.03% | 18.97% | 7.1% | 8.89% | 14.78% | 17.19% | 11.50% | 11.02% |

| CV (%) | 11 | 12 | 13 | 14 | 15 | 16 | 17 | 18 | 19 | 20 |
|---|---|---|---|---|---|---|---|---|---|---|
| Batch 1 (Intra) | 8.80% | 1.72% | 14.90% | 20.02% | 11.73% | 1.24% | 9.05% | 9.91% | 10.76% | 7.13% |
| Batch 2 (Intra) | 8.82% | 7.11% | 11.42% | 17.31% | 5.21% | 5.83% | 15.06% | 7.48% | 7.10% | 4.19% |
| Total (Inter) | 7.88% | 7.84% | 11.95% | 18.02% | 10.26% | 9.26% | 15.03% | 14.80% | 14.27% | 5.38% |

MULTIPLEXED LATERAL FLOW ASSAY FOR DETECTION OF HPV ASSOCIATED CANCER

CROSS-REFERENCE TO RELATED APPLICATIONS

This application claims the benefit of U.S. Provisional Appl. No. 63/247,759 filed Sep. 23, 2021, the entire content of which is incorporated by reference in its entirety.

STATEMENT REGARDING FEDERALLY SPONSORED RESEARCH OR DEVELOPMENT

This invention was made with government support under CA211415 awarded by the National Institutes of Health. The government has certain rights in the invention.

SEQUENCE LISTING

A Sequence Listing accompanies this application and is submitted as an XML file named "2025-10-24_112624.01370_Sequence Listing.xml" which is 8,754 bytes in size and was created on Oct. 24, 2025. The Sequence Listing is incorporated by reference in its entirety.

FIELD

The field of the invention relates to methods and compositions for detecting HPV in a subject sample.

BACKGROUND

Head and neck squamous cell carcinoma (HNSCC), including the oral cavity, oropharynx, larynx, and hypopharynx, is the seventh most common cancer worldwide (1). In the United States, 53,260 were reported in 2020 (2). Occurrence in the oropharyngeal (OP) region has increased yearly (3). About 70% of the patients with oropharyngeal squamous cell cancer are associated with human papillomavirus (HPV). Recognition of type 16 biomarker subtype has significantly changed therapeutic approaches in the past decade (4, 5). Use of p16 immunohistochemistry (IHC) is common for detection of HPV in HNSCC since p16 protein expression is highly correlated with HPV status. However, there are challenges to interpretation, as sometimes the tumors od not stain strongly for p16. Therefore, direct detection of HPV16 is more specific than p16 IHC (6-8). Numerous studies have shown that HPV16 DNA can be detected in HPVOPC using real-time PCR and in-situ hybridization (ISH) (5, 9, 10). However, diagnosis of HPV infection by DNA-based methods may not be reliable because infections are usually transient (11, 12). Therefore, serum antibodies to HPV16 antigens have emerged as promising biomarkers for detection of HNSCC (13-15).

Serological screening has gained interest in the past few years for HPV positive HNSCC. According to the literature, HPV16 E6 seropositivity has the highest sensitivity followed by E2 and E7 in HPVOPC (16) and it has been identified as a potentially early biomarker for HPVOPC (17-19). In addition, previously studies demonstrated that HPV 16 E6 and E7 antibody levels as potential biomarkers for surveillance of HPV-OPC after treatment. Recurrent patients had significantly higher serum antibodies against the HPV16 E6 and E7 proteins than nonrecurrent patients over the follow up period (16, 17). However, HPV serology currently requires laboratory-based tests that are difficulty to implemented for large scale serological studies, or as a point-of-care option.

BRIEF DESCRIPTION OF THE DRAWINGS

FIG. 10A-FIG. 10B. Is a table of the reproducibility of lateral flow assays. (A) Intra- and inter-assay variability between slides and batches. * 1-6 refers to participant ID's. (B) Intra- and inter-assay variability between slides and batches. * 1-20 refers to participants ID's

SUMMARY

Figure 1:
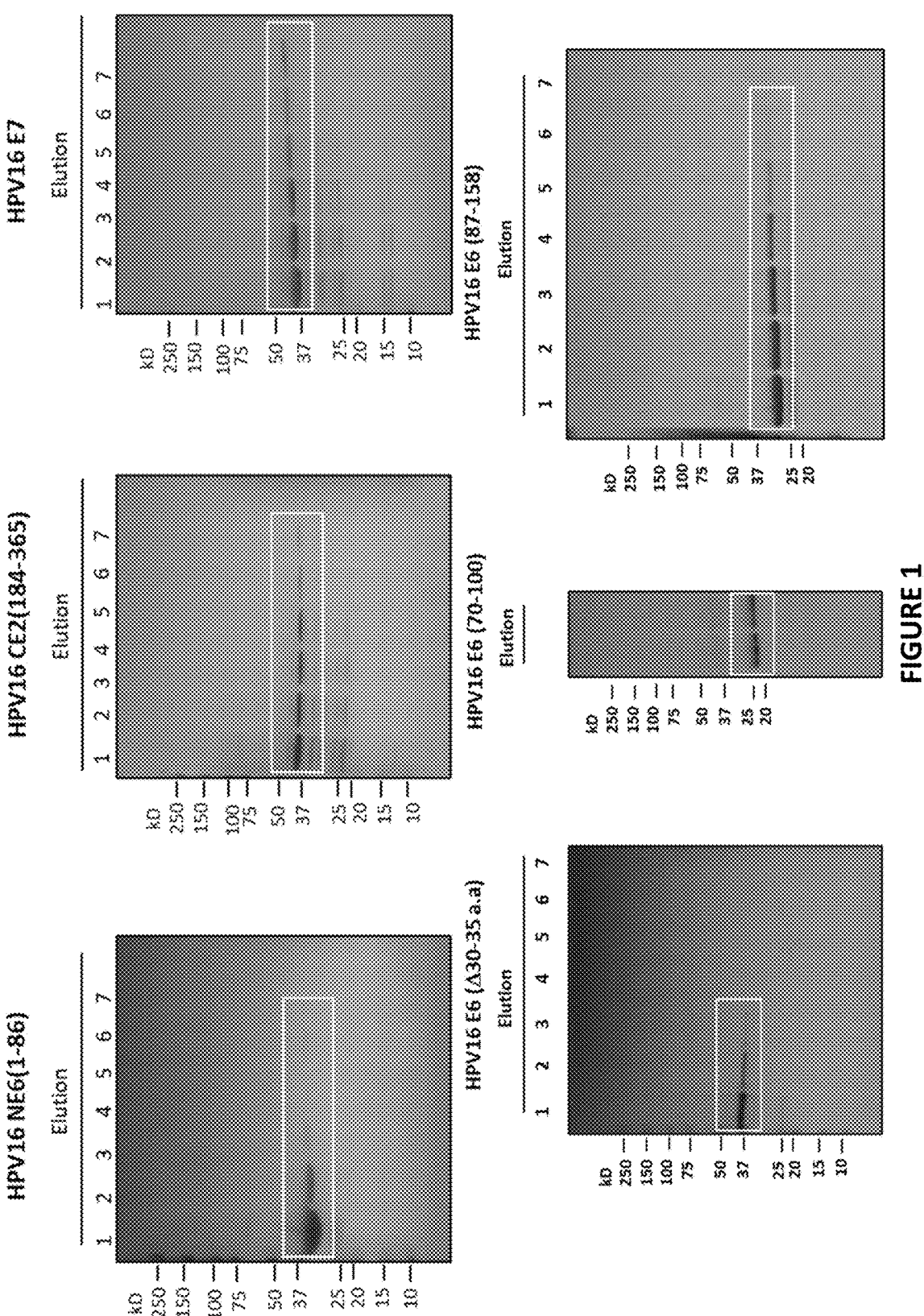
FIG. 1. Expression and solubility of different HPV16 proteins. SDS-PAGE showing the expression and solubility profile of HPV16 proteins. Lane 1-7 are elution fractions.

Disclosed herein are methods, compositions, and kits useful to detect HPV infection in a subject in need thereof. In some embodiment, HPV16 is detected. In some embodiments, the subject has cancer, such as head and neck cancer.

Disclosed herein are compositions. In some embodiments, the compositions comprise comprises one or more of (a)-(c): (a) one or more HPV16 E6 variant polypeptides, wherein the variant polypeptide is selected from the group consisting of: HPV16 E6 (Del30-35), HPV16 E6 (70-100), HPV16 E6 (87-158), and HPV16 E6 (1-86); (b) HPV16 CE2 polypeptide comprising SEQ ID NO: 4, and (c) HPV E7 polypeptide. In some embodiments, the HPV16 CD2 polypeptide comprises or consists of SEQ ID NO: 4. In some embodiments, the HPV16 E7 polypeptide comprises or consists of SEQ ID NO: 2. In some embodiments, the compositions comprises each of the HPV16 E6 variants of (a). In some embodiments, the polypeptides of the composition are linked to a solid support.

Also disclosed herein are nucleic acids encoding the polypeptides of the composition. Also disclosed herein are vectors comprising the nucleic acids encoding the polypeptides of the composition. In some embodiments, the vector comprises an expression vector, such as pDEST15.

Also disclosed herein are cells comprising the polypeptides of the composition, the nucleic acids encoding the polypeptides of the composition, and/or vectors carrying the nucleic acids encoding the polypeptides of the composition. In some embodiments, the cells are prokaryotic cells, such as an *E. coli* cell. In some embodiments, the cells comprise eukaryotic cells, such as a yeast cell, a plant cell, or a mammalian cell. In some embodiments, the cell expresses the encoded HPV polypeptide.

Also disclosed herein are methods for detecting HPV antibodies in a subject in need thereof. In some embodiments, the methods comprises: (a) contacting an antibody-containing sample from a subject to the composition comprising one or more of the polypeptide disclosed herein to form a binding reaction; (b) incubating the binding reaction under conditions to allow antibody to bind the HPV16 polypeptides and form a polypeptide-antibody complex; (c) detecting the complex. In some embodiments, detecting the complex comprises contacting the complex with a detection reagent, wherein the detection reagent comprises a detectable label, and wherein the detection reagent binds the complex. In some embodiments, the detectable label comprises a fluorescent label. In some embodiments, the detection reagent comprises an antibody. In some embodiments, the composition (polypeptides) of step (a) is linked to a solid support. In some embodiments, the solid support comprises a multi-well plate, a test strip, such as, for example, nitrocellulose or cellulose acetate, a glass slide, or microbeads. In some embodiments, the subject sample comprises one or more of blood, serum, plasma, sputum, lymph, and cerebrospinal fluid. In some embodiments, about 1 to about 100 μl of the subject sample is contacted at step (a). In some embodiments, about 1-10 μl of the subject sample is contacted at step (a). In some embodiments, about 1 μl of a subject sample is contacted at step (a).

In some embodiments, compositions (e.g., polypeptides of HPV16) are linked to a solid support, such as a multi-well plate or a test strip, such as nitrocellulose or cellulose acetate, e.g., and are configured for a lateral flow assay.

DETAILED DESCRIPTION

The present invention is described herein using several definitions, as set forth below and throughout the application.

Unless otherwise specified or indicated by context, the terms "a", "an", and "the" mean "one or more." For example, "an antigen" should be interpreted to mean "one or more antigens."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the term "subject" may be used interchangeably with the terms "patient" or "individual" and means an animal, which may be a human or non-human animal. A "subject in need thereof" may include a subject having or at risk of disease or disorder. In some embodiments, a subject has or is at risk of a cancer, such as head or neck cancer.

As used herein, a "subject sample" refers to a biological sample from the subject, and includes but is not limited to blood, serum, plasma, sputum, lymph, and cerebrospinal fluid. In some embodiments, the sample comprises an antibody containing sample.

As used herein, the terms "peptide," "polypeptide," and "protein," refer to molecules comprising a chain (polymer) of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, iso-
leucine, lysine, leucine, methionine, asparagine, proline,
glutamine, arginine, serine, threonine, valine, tryptophan,
and tyrosine residues. The term "amino acid residue" may
include alpha-, beta-, gamma-, and delta-amino acids.

A "full length" polynucleotide sequence is one containing
at least a translation initiation codon (e.g., methionine)
followed by an open reading frame and a translation termi-
nation codon. A "full length" polynucleotide sequence
encodes a "full length" polypeptide sequence.

"Homology" refers to sequence similarity or, interchange-
ably, sequence identity, between two or more polypeptide
sequences. Homology, sequence similarity, and percentage
sequence identity may be determined using methods in the
art and described herein.

The proteins disclosed herein may include "wild type"
proteins and variants, mutants, and derivatives thereof. As
used herein the term "wild type" is a term of the art
understood by skilled persons and means the typical form of
an organism, strain, gene or characteristic as it occurs in
nature as distinguished from mutant or variant forms. As
used herein, a "variant, "mutant," or "derivative" refers to a
protein molecule having an amino acid sequence that differs
from a reference protein or polypeptide molecule. A variant
or mutant may have one or more insertions, deletions, or
substitutions of an amino acid residue relative to a reference
molecule. A variant or mutant may include a fragment of a
reference molecule. For example, a mutant or variant mol-
ecule may include one or more insertions, deletions, or
substitution of at least one amino acid residue relative to a
reference polypeptide.

Regarding proteins, a "deletion" refers to a change in the
amino acid sequence that results in the absence of one or
more amino acid residues. A deletion may remove at least 1,
2, 3, 4, 5, 10, 20, 50, 100, 200, or more amino acids residues.
A deletion may include an internal deletion and/or a terminal
deletion (e.g., an N-terminal truncation, a C-terminal trun-
cation or both of a reference polypeptide). A "variant,"
"mutant," or "derivative" of a reference polypeptide
sequence may include a deletion relative to the reference
polypeptide sequence.

Regarding proteins, "fragment" is a portion of an amino
acid sequence which is identical in sequence to but shorter
in length than a reference sequence. A fragment may com-
prise up to the entire length of the reference sequence, minus
at least one amino acid residue. For example, a fragment
may comprise from 5 to 1000 contiguous amino acid resi-
dues of a reference polypeptide, respectively. In some
embodiments, a fragment may comprise at least 5, 10, 15,
20, 25, 30, 40, 50, 60, 70, 80, 90, 100, 150, 250, or 500
contiguous amino acid residues of a reference polypeptide.
Fragments may be preferentially selected from certain
regions of a molecule. The term "at least a fragment"
encompasses the full-length polypeptide. A fragment may
include an N-terminal truncation, a C-terminal truncation, or
both truncations relative to the full-length protein. A "vari-
ant," "mutant," or "derivative" of a reference polypeptide
sequence may include a fragment of the reference polypep-
tide sequence.

Regarding proteins, the words "insertion" and "addition"
refer to changes in an amino acid sequence resulting in the
addition of one or more amino acid residues. An insertion or
addition may refer to 1, 2, 3, 4, 5, 10, 20, 30, 40, 50, 60, 70,
80, 90, 100, 150, 200, or more amino acid residues. A
"variant," "mutant," or "derivative" of a reference polypep-
tide sequence may include an insertion or addition relative
to the reference polypeptide sequence. A variant of a protein may have N-terminal insertions, C-terminal insertions, inter-
nal insertions, or any combination of N-terminal insertions,
C-terminal insertions, and internal insertions.

Regarding proteins, the phrases "percent identity" and "%
identity," refer to the percentage of residue matches between
at least two amino acid sequences aligned using a standard-
ized algorithm. Methods of amino acid sequence alignment
are well-known. Some alignment methods take into account
conservative amino acid substitutions. Such conservative
substitutions, explained in more detail below, generally
preserve the charge and hydrophobicity at the site of sub-
stitution, thus preserving the structure (and therefore func-
tion) of the polypeptide. Percent identity for amino acid
sequences may be determined as understood in the art. (See,
e.g., U.S. Pat. No. 7,396,664, which is incorporated herein
by reference in its entirety). A suite of commonly used and
freely available sequence comparison algorithms is provided
by the National Center for Biotechnology Information
(NCBI) Basic Local Alignment Search Tool (BLAST),
which is available from several sources, including the NCBI,
Bethesda, MD, at its website. The BLAST software suite
includes various sequence analysis programs including
"blastp," that is used to align a known amino acid sequence
with other amino acids sequences from a variety of data-
bases.

Regarding proteins, percent identity may be measured
over the length of an entire defined polypeptide sequence,
for example, as defined by a particular SEQ ID number, or
may be measured over a shorter length, for example, over
the length of a fragment taken from a larger, defined
polypeptide sequence, for instance, a fragment of at least 15,
at least 20, at least 30, at least 40, at least 50, at least 70 or
at least 150 contiguous residues. Such lengths are exemplary
only, and it is understood that any fragment length supported
by the sequences shown herein, in the tables, figures or
Sequence Listing, may be used to describe a length over
which percentage identity may be measured.

Regarding proteins, the amino acid sequences of variants,
mutants, or derivatives as contemplated herein may include
conservative amino acid substitutions relative to a reference
amino acid sequence. For example, a variant, mutant, or
derivative protein may include conservative amino acid
substitutions relative to a reference molecule. "Conservative
amino acid substitutions" are those substitutions that are a
substitution of an amino acid for a different amino acid
where the substitution is predicted to interfere least with the
properties of the reference polypeptide. In other words,
conservative amino acid substitutions substantially conserve
the structure and the function of the reference polypeptide.
The following table provides a list of exemplary conserva-
tive amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |

-continued

| Original Residue | Conservative Substitution |
|---|---|
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

As used herein, "viral load" is the amount of virus present in the blood of a patient or animal. Viral load is also referred to as viral titer or viremia. Viral load can be measured in variety of standard ways including by plaque assays or copy Equivalents of the viral RNA (vRNA) genome per milliliter blood plasma (vRNA copy Eq/ml). This quantity may be determined by standard methods that include RT-PCR.

As used herein, the term "human papillomavirus" or "HPV" refers to a DNA virus from the Papillomaviridae family. Over 170 types have been described. Nearly all cervical cancer is due to HPV; two strains, HPV16 and HPVl8, account for 70% of cases. HPV16 is responsible for almost 90% of HPV-positive oropharyngeal cancers. Proteins of the Present Disclosure As used herein the term "HPV E6", or "E6" refer to the HPV16 E6 protein. The amino acid sequence of HPV16 E6 is provided below as SEQ ID NO: 1.

MHQKRTAMFQDPQERPRKLPQLCTELQTTIHDIILECVYCKQQLLRREVY

DFAFRDLCIVYRDGNPYAVCDKCLKFYSKISEYRHYCYSLYGTTLEQQYN

KPLCDLLIRCINCQKPLCPEEKQRHLDKKQRFHNIRGRWTGRCMSCCRSS

RTRRETQL

In some embodiments, variants of the E6 protein are provided. By way of example but not by way of limitation, exemplary E6 variants include (1) HPV16 E6 (Del30-35) =HPV16 E6 comprising or consisting of a deletion of amino acids 30-35; (2) HPV16 E6 (70-100), a 31 amino acid fragment of E6 comprising or consisting of amino acids 70-100; (3) HPV16 E6 (87-158), a 72 amino acid fragment of E6 comprising or consisting of amino acids 87-158; and (4) HPV16 E6 (1-86), also termed "NE6" a fragment of E6 comprising or consisting of amino acids 1-86. In some embodiments, the E6 variants are more soluble than the unmodified (wild-type) E6 protein.

As used herein the term "E7" refers to the HPV16 E7 protein, the amino acid sequence of which is shown below as SEQ ID NO: 2.

MHGDTPTLHEYMLDLQPETTDLYCYEQLNDSSEEEDEIDGPAGQAEPDRA

HYNIVTFCCKCDSTLRLCVQSTHVDIRTLEDLLMGTLGIVCPICSQKP

As used herein, the term E2 refers to the HPV16 E2 protein, the amino acid sequence of which is shown below as SEQ ID NO: 3.

METLCQRLNVCQDKILTHYENDSTDLRDHIDYWKHMRLECAIYYKAREMG

FKHINHQVVPTLAVSKNKALQAIELQLTLETIYNSQYSNEKWTLQDVSLE

VYLTAPTGCIKKHGYTVEVQFDGDICNTMHYTNWTHIYICEEASVTVVEG

QVDYYGLYYVHEGIRTYFVQFKDDAEKYSKNKVWEVHAGGQVILCPTSVF

SSNEVSSPEIIRQHLANHPAATHTKAVALGTEETQTTIQRPRSEPDTGNP

CHTTKLLHRDSVDSAPILTAFNSSHKGRINCNSNTTPIVHLKGDANTLKC

LRYRFKKHCTLYTAVSSTWHWTGHNVKHKSAIVTLTYDSEWQRDQFLSQV

KIPKTITVSTGFMSI

In some embodiments, a modified version of E2, is provided in the methods and compositions disclosed herein. By way of example, but not by way of limitation, a fragment of CE2 is provided. In some embodiments, the fragment CE2 comprises SEQ ID NO: 4, as shown below, and as shown by the underlined amino acids in SEQ ID NO: 3, above. In some embodiments, the CE2 variant is more soluble than the wild-type CE2 protein.

WEVHAGGQVILCPTSVFSSNEVSSPEIIRQHLANHPAATHTKAVALGTEE

TQTTIQRPRSEPDTGNPCHTTKLLHRDSVDSAPILTAFNSSHKGRINCNS

NTTPIVHLKGDANTLKCLRYRFKKHCTLYTAVSSTWHWTGHNVKHKSAIV

TLTYDSEWQRDQFLSQVKIPKTITVSTGFMSI

Assay Compositions Comprising the Proteins of the Present Disclosure; Exemplary Methods of Use Human papillomavirus (HPV) is a pathogen virus which is related with different cancers, including cervical cancer and head and neck cancer. Over 100 types of HPV have been identified and divided into high and low risk groups of causing cervical cancer. 70% of cervical cancer is caused by HPV16/H1PV18 and 90% of HPV DNA-positive head and neck cancer is HPV16. Additionally, a lot of studies report that HPV16 E6/E7/E2 antibodies could be detected as biomarkers in both cervical cancer and head and neck cancer. However, HPV serology currently requires laboratory-based tests that are difficult to implemented for large scale serological studies. Therefore, development of a point-of-care assay for the detection of multiple HPV-specific IgG serologic biomarkers is an efficiency way for diagnostics diseases in low and middle-income countries (LMICs) and patients who live under limited resource environments such as primary care or resource-constrained places.

There are several challenges to point of-care serology for HPV16. First, the point of-care platform should be able to detect to multiple markers on a single device, but existing point-of care device can typically only detect a single biomarker. Second, serology testing depends on the immune system recognizing an antigen/protein and triggering an immune response. Antigen/protein stability and purity are critical parameters for developing a point of-care platform. Third, point of care test results may not be as sensitive or specific as lab based test results. As a solution, and as described herein, we purified E6, CE2, and full length of E7 and developed a rapid, inexpensive, multiplex, and user-friendly detection for HPV associated cancers.

The prior art serological methods, including ELISA, all depend on purified HPV proteins, and HPV16 E6 has always presented a purification challenge from bacteria due to hydrophobic regions on the protein leading to an insoluble protein product. There are three predicted hydrophobic regions of HPV16 E6, amino acids 30-35 (IHDIIL) SEQ ID NO: 5, amino acids 58-62 (LCIVY) SEQ ID NO: 6, and amino acids 104-108 (LCDLLI) SEQ ID NO: 7. As disclosed herein, the present inventors have solved the purification problem by making different versions of HPV16 E6 to obtain a soluble form. In some embodiments, a purification vector, pDEST15 was used (see e.g., Rosenberg, A. H., Lade, B. N., *Chui*, D.-S., Lin, S.-W., Dunn, J. J., and Studier, F. W. (1987) Vectors for Selective Expression of Cloned DNAs by T7 RNA Polymerase. Gene 56, 125-135; Studier, F. W., and Moffatt, B. A. (1986) Use of Bacteriophage T7 RNA Polymerase to Direct Selective High-Level Expression of Cloned Genes. J. Mol. Biol. 189, 113-130; Studier, F. W., Rosenberg, A. H., Dunn, J. J., and Dubendorff, J. W. (1990) Use of T7 RNA Polymerase to Direct Expression of Cloned Genes. Meth. Enzymol. 185, 60-89; Landy, A. (1989) Dynamic, Structural, and Regulatory Aspects of Lambda Site-specific Recombination. Ann. Rev. Biochem. 58, 913-949, each of which is incorporated herein by reference in its entirety), without co-transfection of chaperone plasmid.

Disclosed herein are four different versions of an HPV16 E6 soluble protein, HPV16 E6 (Del30-35), HPV16 E6 (70-100), HPV16 E6 (87-158), and HPV16 E6 (1-86). These four different variants of HPV16 E6 have been verified using ELISA assay. One of these HPV16 E6 proteins, HPV16 E6 (1-86), not only has a high yield with respect to protein production but also has shown seropositivity to HPV positive plasma/sera. In addition, this variant does not have a high background signal in the presence of HPV positive samples.

In some embodiments, the HPV16 proteins E6 (or variants thereof, e.g., modified as described above), E7 (or variants thereof), and CE2 (or variants thereof) are linked to a solid support.

In some embodiments, the solid support comprises a multi-well plate, such as a 96-well plate or a 384-well plate, e.g., for use in an enzyme-linked immunosorbent assay (ELISA).

In some embodiments, the solid support comprises a test strip, e.g., for use in a lateral flow assay. In some embodiments, the lateral flow assay is in multiplex format, wherein a single assay can detect the presence of E6, E7, and/or CE2 antibodies in a subject sample.

In some embodiments, the lateral flow assay is in sandwich format; in some embodiments, the lateral flow assay is in competitive format. In some embodiments, the test strip is provided in a cartridge.

In some embodiments, the test strip comprises nitrocellulose, or cellulose acetate.

The methods and compositions disclosed herein are useful for the detection of HPV16 infection in a subject in need thereof. In some embodiments, the subject may be harboring and HPV16 infection. In some embodiments, the subject may have a cancer, such as a head and/or neck cancer.

Exemplary Advantages and Applications

Some point-of-care (POC)-based platforms developed to detect HPV antibody in plasma or blood are commercially available.

For example, the OncoE6TM Oral test from Arbor Vita is a lateral flow test device used to detect the presence of E6 proteins from HPV16 and HPV18. However, the test usually takes 2.5 hours which is long for a POC test. Second, Cobas HPV PCR testing from Roche identifies genotypes 16 and 18, and other 12 high-risk HPV genotypes as well. However, this test is limited to use the Cobas×480 instrument and the Cobas z 480 analyzers. No other sample preparation instrument or PCR system can be compatible with this test. Furthermore, DNA testing cannot discriminate between transient and persistent HPV infections since most HPV infections are transient and the immune system usually eliminates the virus in 12-36 months. A third example is the Aptima HPV testing from Hologic that measures E6/E7 mRNA of 14 high-risk HPV genotypes using real-time amplification. This system can run up to 250 tests in about five hours in a laboratory setting environment; this cannot be considered a point of care testing and is difficult to reproduce on a clinical site.

Other devices or kits have been developed to detect and quantify anti-HPV E7 antibody. However, the multiplexing capability of many of these assays is limited. Another study developed a luciferase-based detection (luciferase immuno-precipitation system) of HPV16 E2, E6, and E7 antibodies, but this assay is time consuming, taking approximately 2.5 hours to finish, which might be prohibitive in some circumstances.

Disclosed herein, the inventors provide not only a rapid, inexpensive, and user friendly fluorescent serological lateral flow assay for HPV POC, but also a multiplex format. In embodiments, the assay requires less than 1 ul of plasma/serum to test three HPV antigens at the same time.

EXAMPLES

Abstract

Human papillomavirus (HPV) type 16 is associated with the majority of oropharyngeal carcinomas (OPC). Antibodies (Abs) to multiple HPV16 early antigens, including E2, E6, and E7 have been detected in patient sera, and are strongly associated with risk for OPC. However, HPV serology currently requires laboratory-based tests that are difficulty to implemented for large scale serological studies.

Here, we have developed the first multiplexed point-of-care assay for the serological detection of HPV16 E6, E7, and E2 antibodies using a fluorescent based lateral flow assay (LFA) platform. We measured Abs to HPV16 E2, E6, and E7 by point of care LFA in sera from 119 cases, 41 partners, and 81 healthy volunteers from HOTSPOT study. The sensitivity of HPV16 E2, E6, and E7 were 47.9% (57/119), 31.9% (38/119), and 57.1% (68/119). Overall, the sensitivity was 76.5% (91/119) for the combined serological assay, comparable to known laboratory-based assay. This provides a platform for rapid screening of at-risk individuals of HPV-associated HNSCC.

INTRODUCTION

Head and neck squamous cell carcinoma (HNSCC), including the oral cavity, oropharynx, larynx, and hypopharynx, is the seventh most common cancer worldwide (1). In the United States, 53,260 were reported in 2020 (2). It's occurrence in the oropharyngeal (OP) region has increased yearly (3). About 70% of the patients with oropharyngeal squamous cell cancer are associated with human papillomavirus (HPV). Recognition of type 16 biomarker subtype has significantly changed therapeutic approaches in the past decade (4, 5). Use of p16 immunohistochemistry (IHC) is commonly used for detection of HPV in HNSCC since p16 protein expression is highly correlated with HPV status. However, it is difficult to interpret as sometimes the HPV status of tumors is not staining strongly for p16. Therefore, direct detection of HPV16 is more specific than p16 IHC (6-8). Numerous studies have shown that HPV16 DNA can be detected in HPVOPC using real-time PCR and in-situ hybridization (ISH) (5, 9, 10). However, diagnosis of HPV infection by DNA-based methods may not be reliable because infections are usually transient (11, 12). Therefore, serum antibodies to HPV16 antigens have emerged as promising biomarkers for detection of HNSCC (13-15).

Serological screening has gained interest in the past few years for HPV positive HNSCC. According to the literature, HPV16 E6 seropositivity has the highest sensitivity followed by E2 and E7 in HPVOPC (16) and it has been identified as a potentially early biomarker for HPVOPC (17-19). In addition, previously studies demonstrated that HPV 16 E6 and E7 antibody levels as potential biomarkers for surveillance of HPV-OPC after treatment. Recurrent patients had significantly higher serum antibodies against the HPV16 E6 and E7 proteins than nonrecurrent patients over the follow up period (16, 17). Therefore, there is a need for innovative point of-care serological diagnostic device that is sensitive and specific for screening HPV positive HNSCC.

However, there are several challenges to point of-care serology for HPV16. First, the point of-care platform should be able to detect multiple markers on a single device, but existing point-of-care device can typically only detect a single biomarker. Second, serology testing depends on the immune system recognizing an antigen/protein and triggering an immune response. Antigen/protein stability and purity are critical parameters for developing a point of-care platform. Third, point of care test results may not be as sensitive or specific as lab-based test results. As a solution, in this study, we were able to purify NE6, CE2, and full length of E7 and developed a rapid, inexpensive, and user-friendly detection for HPVOPC. It is the first multiplex, serological lateral flow assay for HPVOPC combined with our in-house portable fluorescence reader (18) for detection of antibody of HPV16 CE2, NE6, and E7 using our recombinant proteins. Finally, we evaluated our assay to investigate the serologic immune responses to multiple HPV16 antigens in sera samples from HPVOPC patients. These LFIAs were also tested in the field through finger prick testing on EBNA-1 protein using the whole healthy blood. We believe that this diagnostic test will be potentially useful for identifying HPVOPC patients who are in need of screening but live under limited resource environments such as primary care or resource-constrained places.

Results

Expression and Purification of Proteins

The serological methods including ELISA are all depends on purified HPV proteins and HPV16 E6 always has a challenge of bacterial purification due to hydrophobic region leading to insoluble protein. There are three predication hydrophobic regions of HPV16 E6, amino acids 31-36 (IHDIIL) SEQ ID NO: 5, amino acids 58-62 (LCIVY) SEQ ID NO: 6, and amino acids 104-108 (LCDLLI) SEQ ID NO: 7 (19). There are some purification methods of HPV16 E6 already developed. By way of example, one group co-transfected HPV16 E6 expression vector and the chaperone plasmid into *E. coli* in order to get soluble protein (20). Another research group also got soluble of HPV16 E6 protein and had binding ability to p53 by deleting one hydrophobic amino acid region 31-36 (IHDIIL) SEQ ID NO: 5 into pGEX4T1 vector (19). In this study, we solved the purification problem by making different versions of HPV16 E6 to obtain it in the soluble form using the purification pDEST15 vector without co-transfection of chaperone plasmid. Next, we investigated if these purified proteins have ability to detect and distinguish anti-HPV16 E6 antibody from HPVOPC and control samples. The first two constructs express a deletion hydrophobic region of HPV16 E6 (A30-35 a.a) (19), and the region of amino acids 70-100 which excludes these three predication hydrophobic regions. Besides, one region ($^{91}$YGTTL$^{95}$) SEQ ID NO: 8 of HPV16 E6 is a highly conserved epitope (YGD/XTL) among various HPVs E6 which has already identified as B-cell epitopes in HPV58 E6 (21). Therefore, we truncated HPV16 E6 into two regions. One is C-terminal of E6 (87-158) which has highly conserved epitope ($^{91}$YGTTL$^{95}$) SEQ ID NO: 8 and the other one is N-terminal of E6 (1-86). The IPTG induced expression of different versions of HPV16 E6 proteins and other HPV16 CE2 and HPV16 E7 were in fusion with the N-terminal GST as seen in the Coomassie brilliant blue stained SDS-PAGE (FIG. 1).

Recombinant Protein Evaluation by ELISA

Figure 2A:
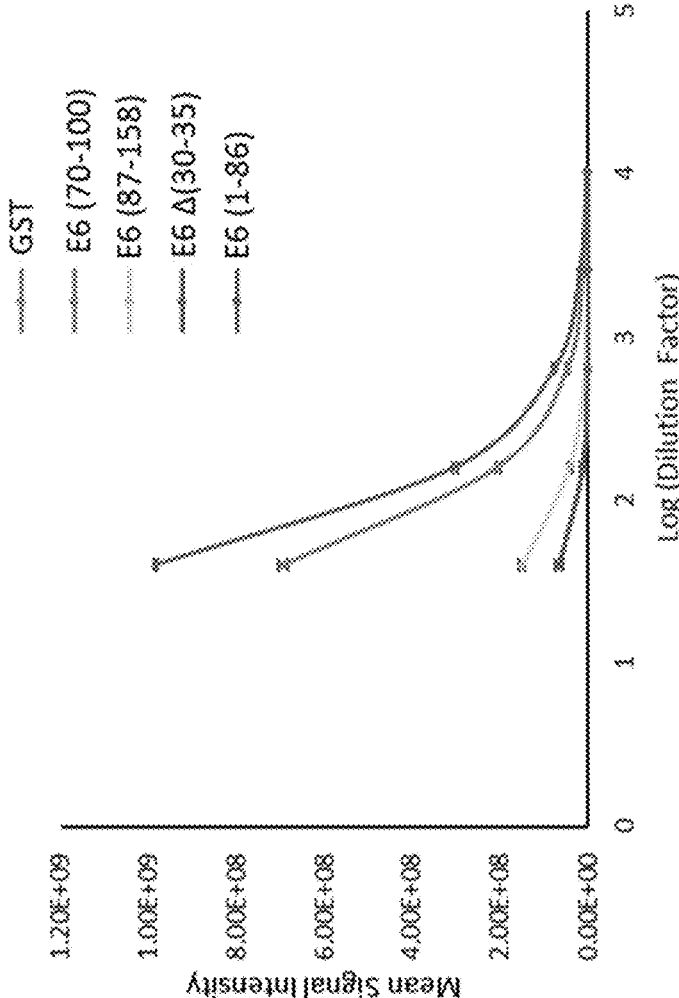
FIG. 2A-FIG. 2C. Different versions of HPV16 recombinant proteins evaluation by ELISA. (A) Different versions of HPV16 E6 (B) HPV16 E7 (C) HPV16 CE2 recombinant proteins were coated on a 96-well plate and incubated with serially diluted case and control sera, followed by anti-human IgG HRP antibody.

ELISAs were used to preliminarily evaluate the recombinant proteins. First, we investigated the background reactivity to these different versions of HPV16 E6 proteins using control serum. HPV16 E6(D30-35 a.a), E6(1-86), E6(70-100), and E6(87-158) were coated on a 96-well plate and detected the signal from serial dilutions of negative sample (control) using anti-human IgG antibody conjugated with HRP. From FIG. 2A, E6(70-100) and E6(Del30-35 a.a) have strong background signals from the control serum. N-terminal of HPV16 E6 was selected since its signal is similar as GST control. We found out that N-terminal of E6 (1-86) has not only has a high yield of protein production but also has shown seropositivity to HPVOPC plasma/sera. Also, it does not have a high background signal in the partners of HPVOPC samples, not like C-terminal of E6.

Figures 2B, 2C:
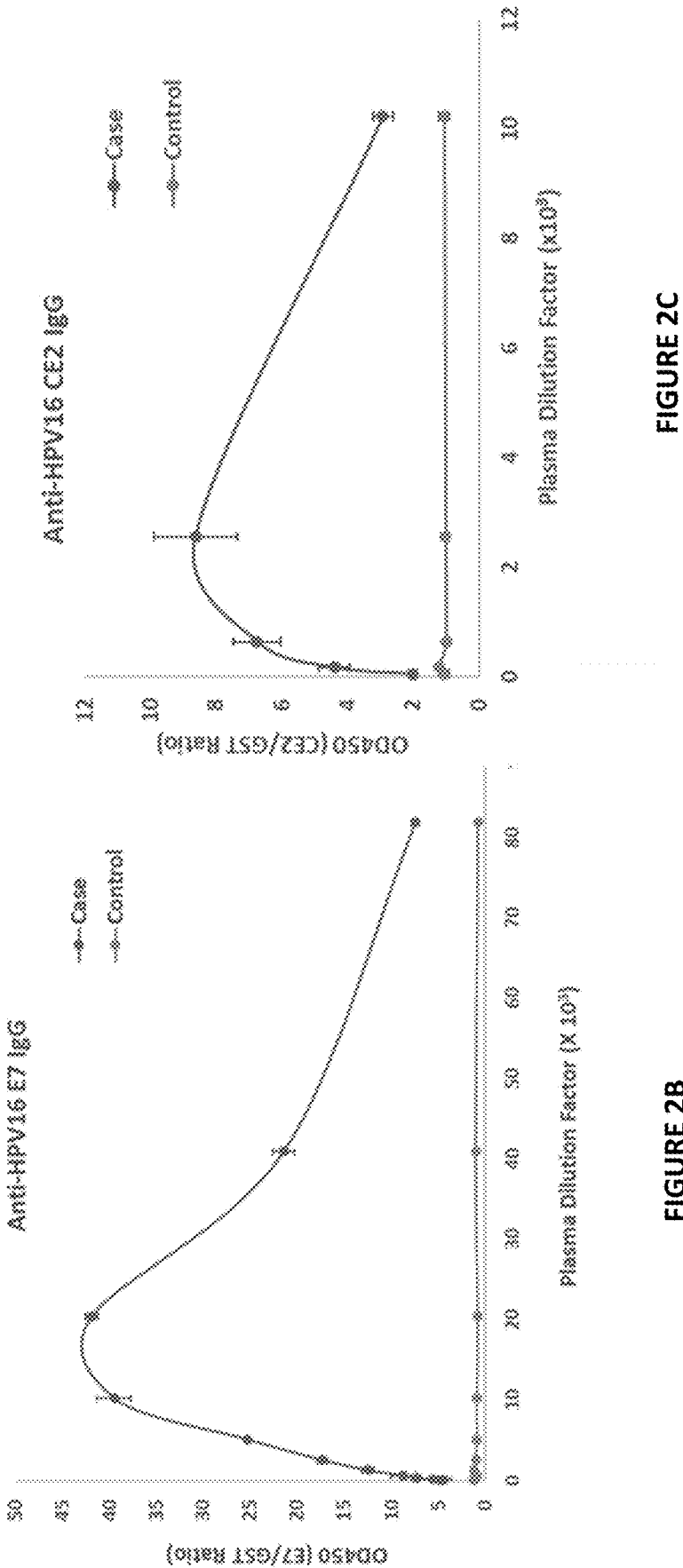
Figure 3:
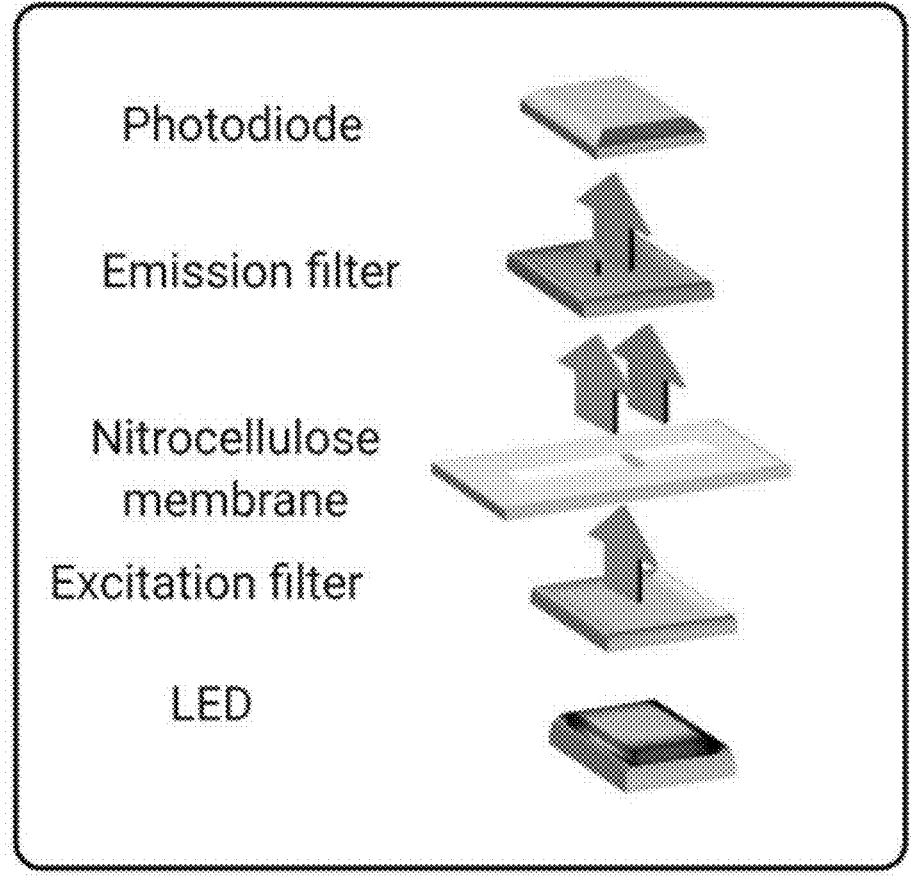
FIG. 3. Circuit schematic inside the reader showing charge-integration amplifier readout circuit, biorecognition sites on a microscope slide and LEDs used as the excitation source.
Figure 3:

Next, we evaluated the recombinant HPV16 CE2 and HPV 16 E7 proteins as well using samples at a serial of dilutions. From FIG. 2B&3C, both HPV16 CE2 and HPV16 E7 proteins had lower background values in negative sample and higher signal in case sample. In addition, the IgG-specific signals of HPV16 CE2 and HPV 16 E7 for ELISA at high dilution are higher than those at low dilution in some cases, mostly because of the hook effect. Finally, HPV16 NE6(1-86), HPV16 CE2, and HPV 16E7 were chosen to be dispensed on the nitrocellulose for test lines of lateral flow assay.

Evaluation of Lateral Flow Assay

Figure 4:
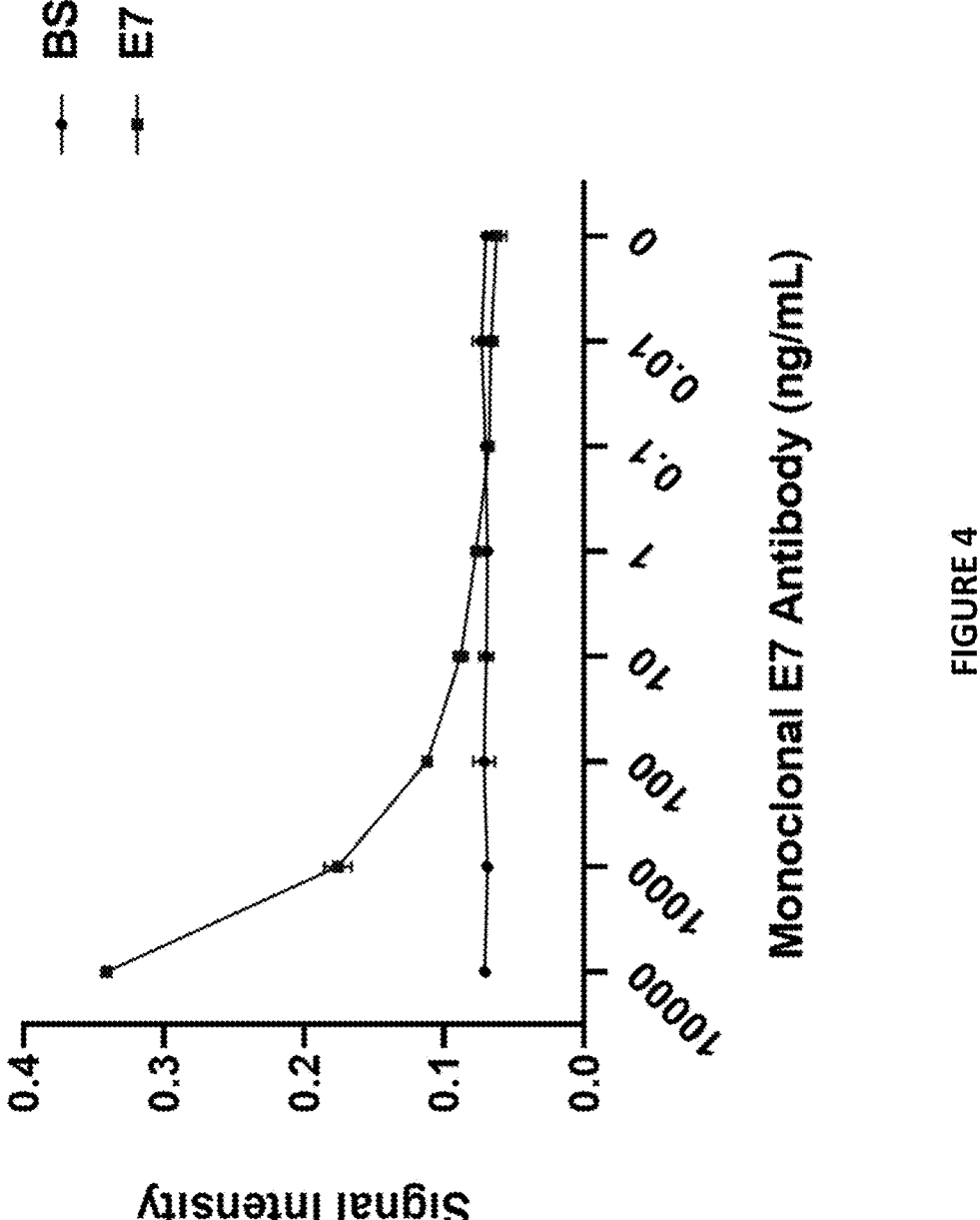
FIG. 4. Limit of detection of the lateral flow assay. LoD was obtained by comparing signal intensity in plasma spiked different concentration of monoclonal HPV16 E7 antibody and negative control.
Figures 7A, 7B, 7C:
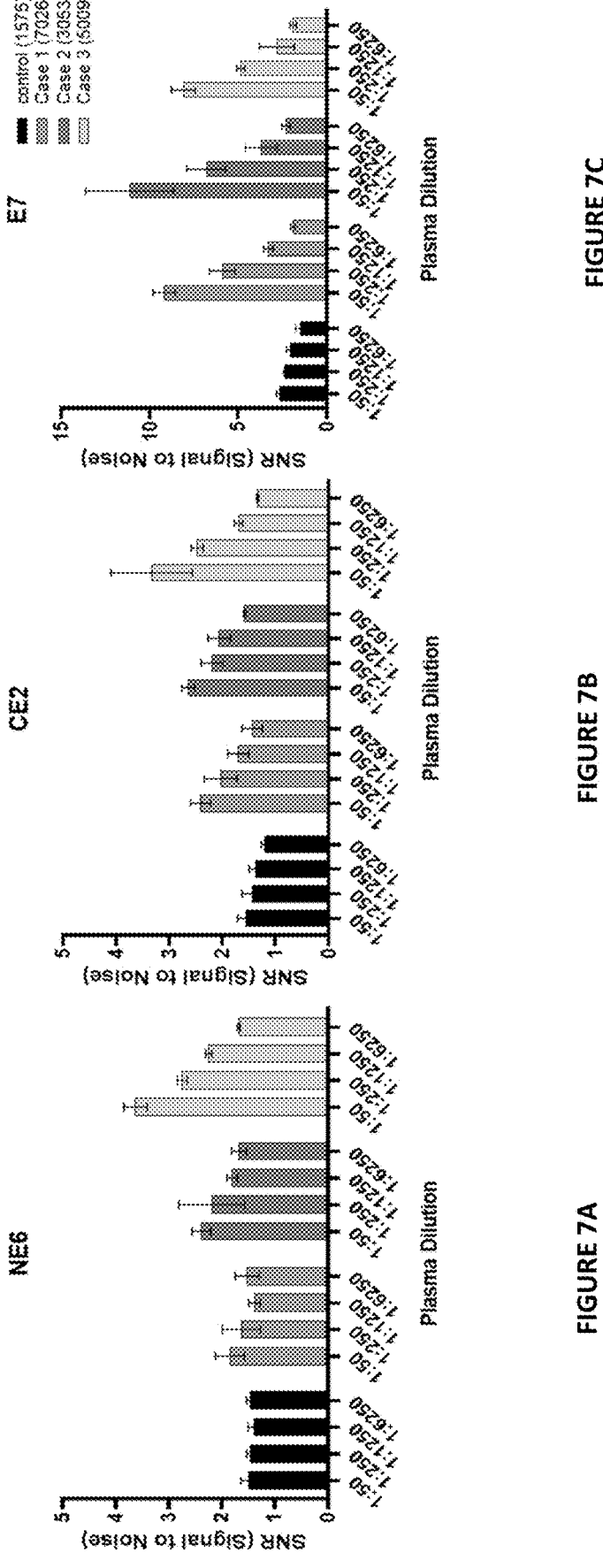
FIG. 7A-FIG. 7C. Evaluation of lateral flow assay. The anti-HPV IgG lateral flow assay system was evaluated using a serial dilution of sera samples at $1/10$, $1/50$, $1/250$, $1/1250$, and $1/6250$ collected from HOTSPOT and the result of (A) HPV16 NE6, (B) HPV16 CE2, and (C) HPV16 E7 were measured by the reader.

BSA (negative control) and IgG (positive control) were dispensed as well as HPV 16E6(1-86), HPV 16CE2, and HPV 16E7 on five sites spaced at 6 mm intervals on the same nitrocellulose strip. After assembling test strips, we tested the performance of immunoassay in clinical samples. First, the anti-HPV IgG lateral flow assay system was evaluated using a serial dilution of sera samples at $\frac{1}{10}$, $\frac{1}{50}$, $\frac{1}{250}$, $\frac{1}{1250}$, and $\frac{1}{6250}$ collected from HOTSPOT and the results were measured by the reader mentioned previously (FIG. 3). Three cases and one control samples were confirmed positive by RAPID ELISA. As shown in FIG. 7, the signal of HPV16 NE6, HPV16 CE2, and HPV 16E7 still can be detected by the reader from $\frac{1}{50}$ to $\frac{1}{250}$ dilution in all three cases and there is no significant signal detected in the control sample. Some samples even can be detected anti-HPV 16E7 IgG signal at $\frac{1}{1250}$ dilution. Second, we spiked various concentrations of anti-HPV16 E7 antibody ranging from 0.01 ng/mL to 10 µg/mL into negative control plasma. As a result, we observed 10 ng/mL of anti-HPV16 E7 antibody concentration provided different signal intensity compared to the negative control (FIG. 4).

Figures 8A, 8B, 8C:
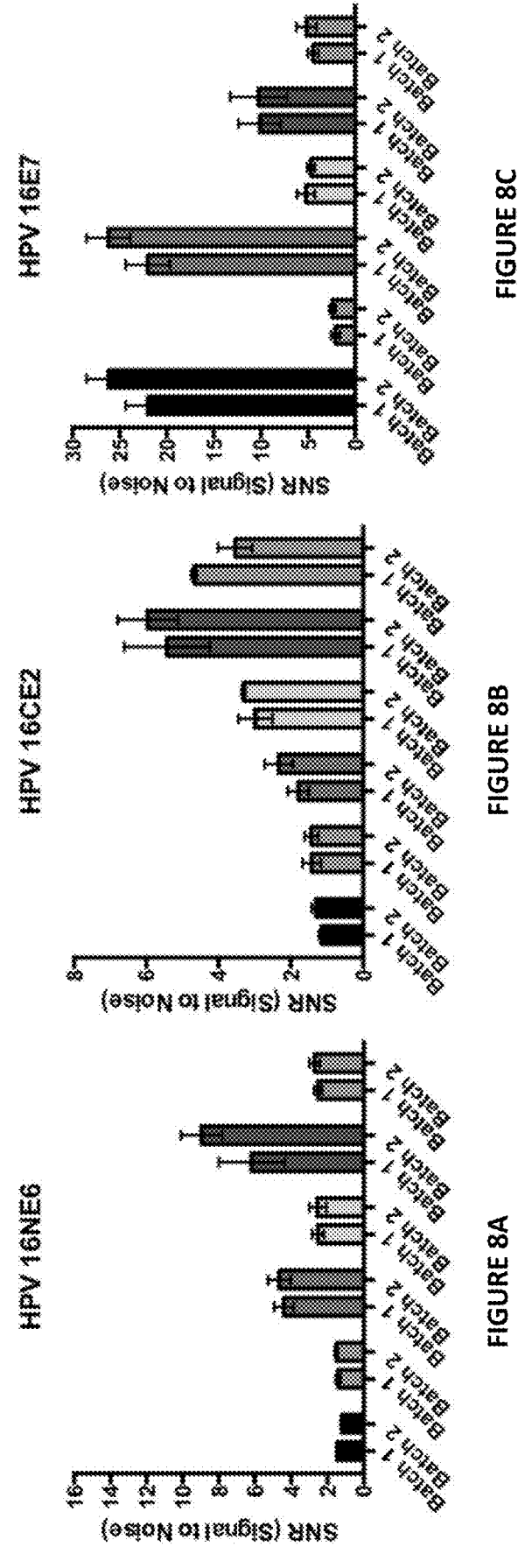
FIG. 8A-FIG. 8C. The reproducibility of lateral flow assay from two batches. The reproducibility of lateral flow assay was evaluated by 6 different sera samples.

Next, it is crucial in quantitative lateral flow assays to achieve repeatability. Therefore, lateral flow assay was evaluated for reproducibility as well. According to the data, there was no more than a 2-fold difference in the variation of anti-HPV IgG detection between slides and printing batches analyzed and processed at different times for 6 samples (FIG. 8).

Figure 9:
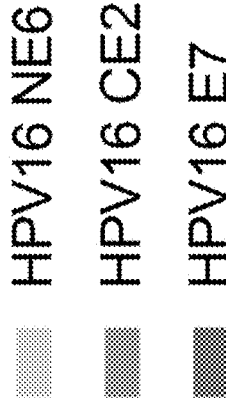
FIG. 9. The reproducibility of lateral flow assay at room temperature storage. The reproducibility of lateral flow assay was evaluated up to 4 months at room temperature storage.
Figure 9:
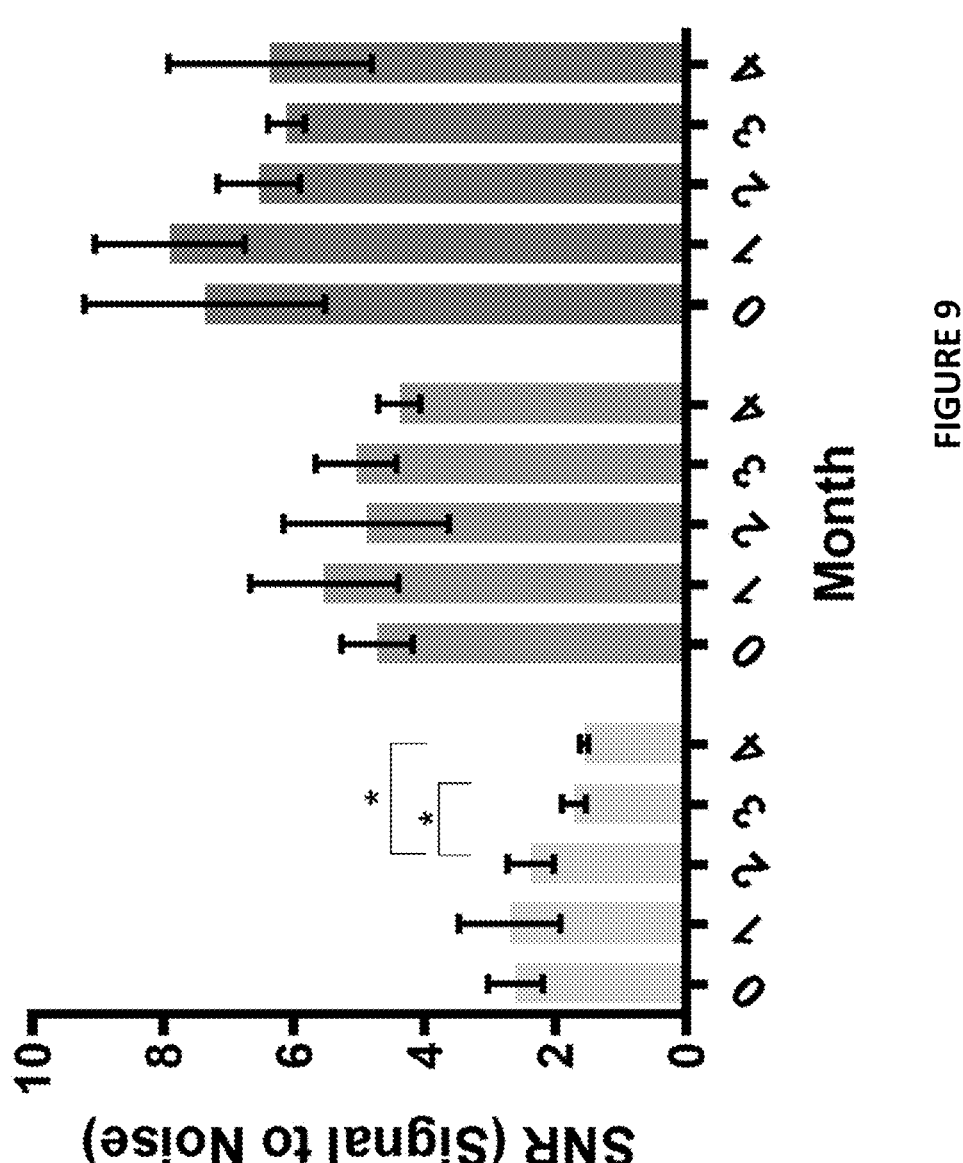

The storage of the assay strips is one of the most important factors in quality assurance for the strips and its repeatability. We have already investigated the temperature did not affect our assay when we compared the condition of storage at 4° C. and room temperature for three weeks (22). Here, we investigated whether room temperature of the strip during storage affects the performance, HPV16 NE6, HPV16 CE2, and HPV16 E7 were dispensed on the strips as well as a BSA negative control line and IgG positive control line. The strips were sealed in different bags with desiccants using a vacuum sealer machine. The strips were stored at room temperature (25° C.) and we ran the experiments every month to compare whether the signal decreases during long term storage. The signals from the strips kept at room temperature can still be detected even after two months of storage and the signals of HPV16 NE6 from strips stored for 3 months at RT were significantly decreased than those strips stored for two months. The test strips seem stable for up to 2 months at RT (FIG. 9).

HPV16 Antibody Prevalence

Figure 5B:
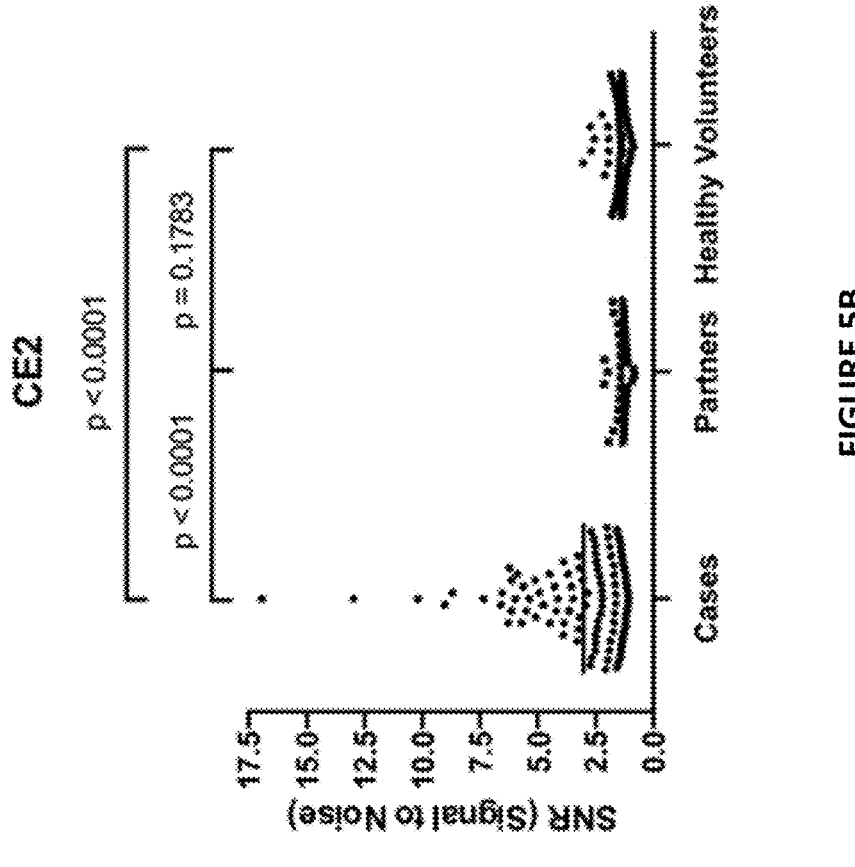
FIG. 5A-FIG. 5C. Detection of HPV16 antibodies in serum from 116 HPVOPC cases, 41 partners, and 81 controls. The signal to noise of IgG to specific HPV16 protein/control BSA protein detected in sera is shown. The black line in each group represents the median value in that group. HPV16-specific Abs to (A) NE6, (B) CE2, and (C) E7 are detected in sera from patients with HPVOPC compared to partners and controls. Comparisons of SNR between control and case group were performed using Mann-Whitney nonparametric analysis (GraphPad Prism).
Figure 5A:
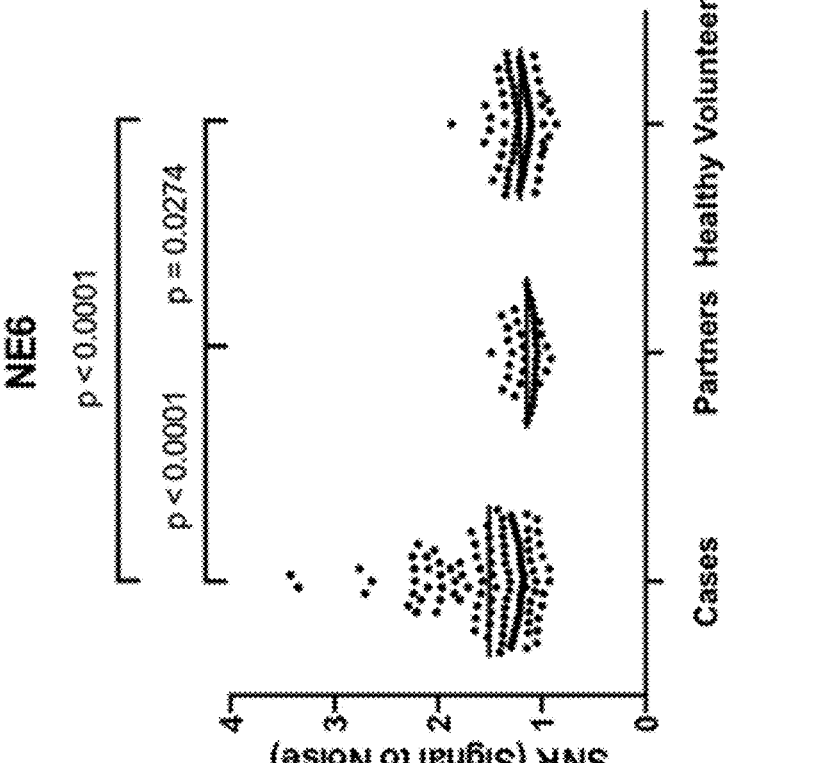
Figure 5C:
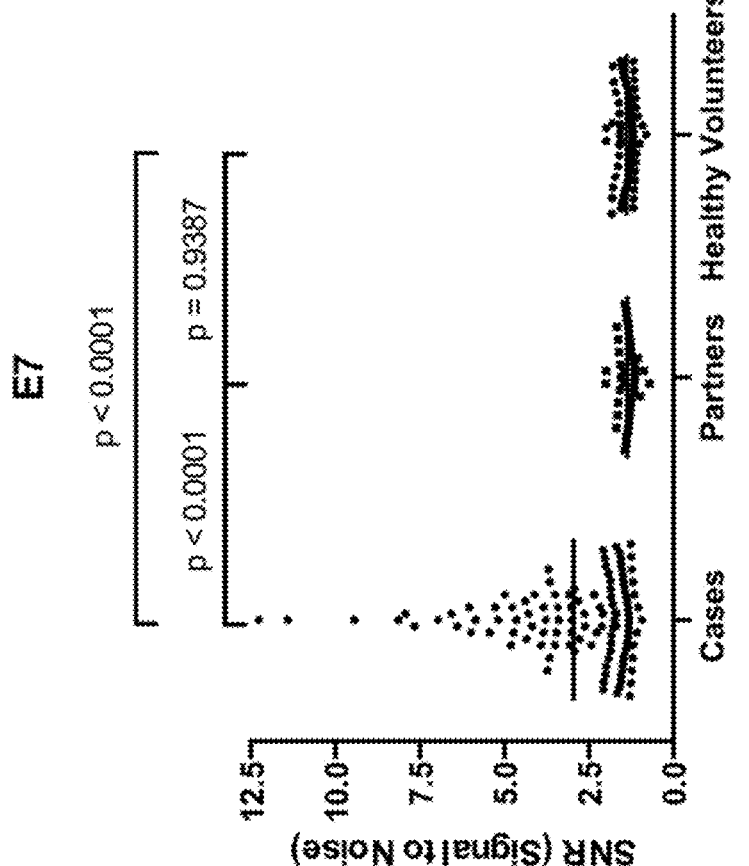
Figure 6B:
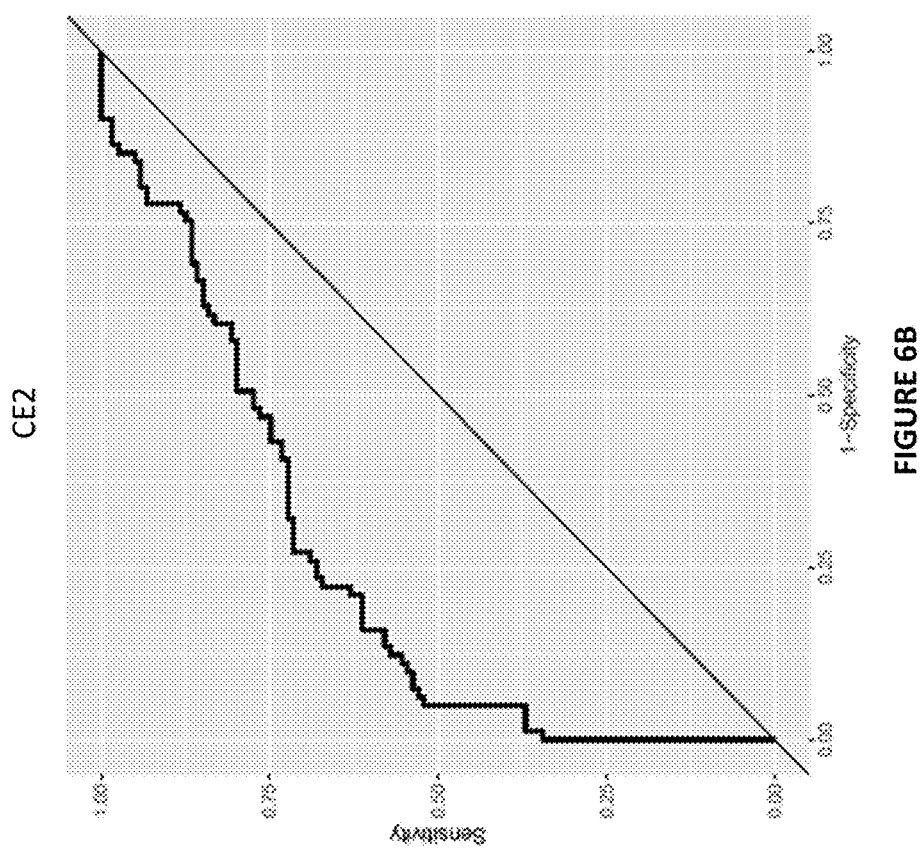
FIG. 6A-FIG. 6D. ROC curves of HPV serology. Individual biomarker performance (A) NE6, (B) CE2, (C) E7 was shown, as well as the (D) combined parts.
Figure 6A:
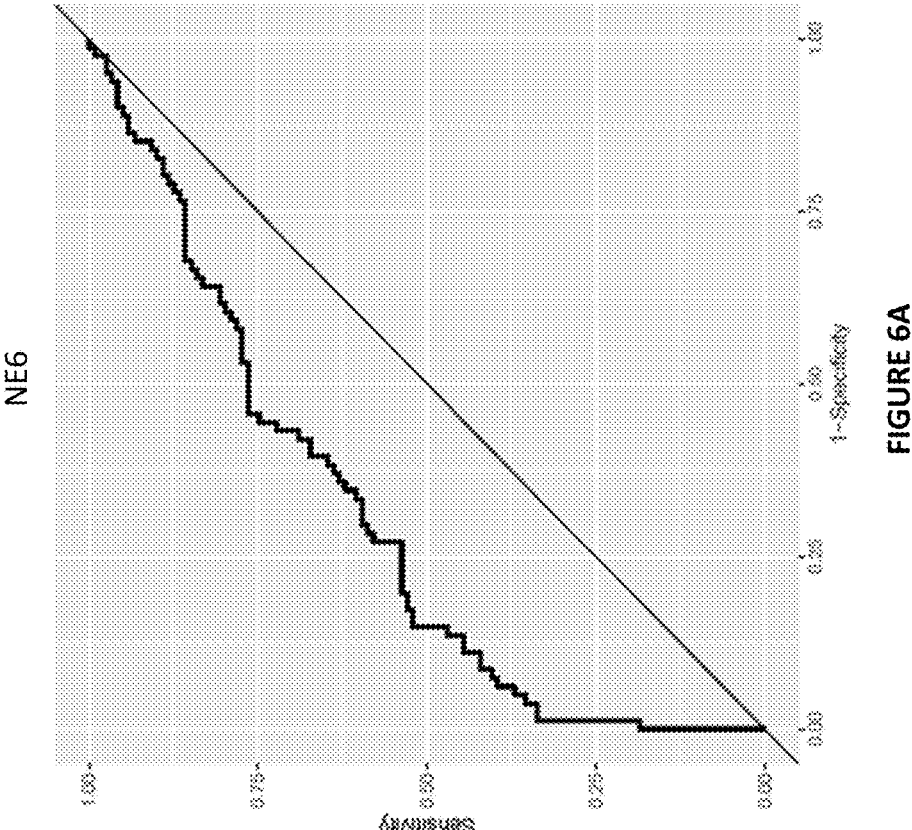
Figure 6D:
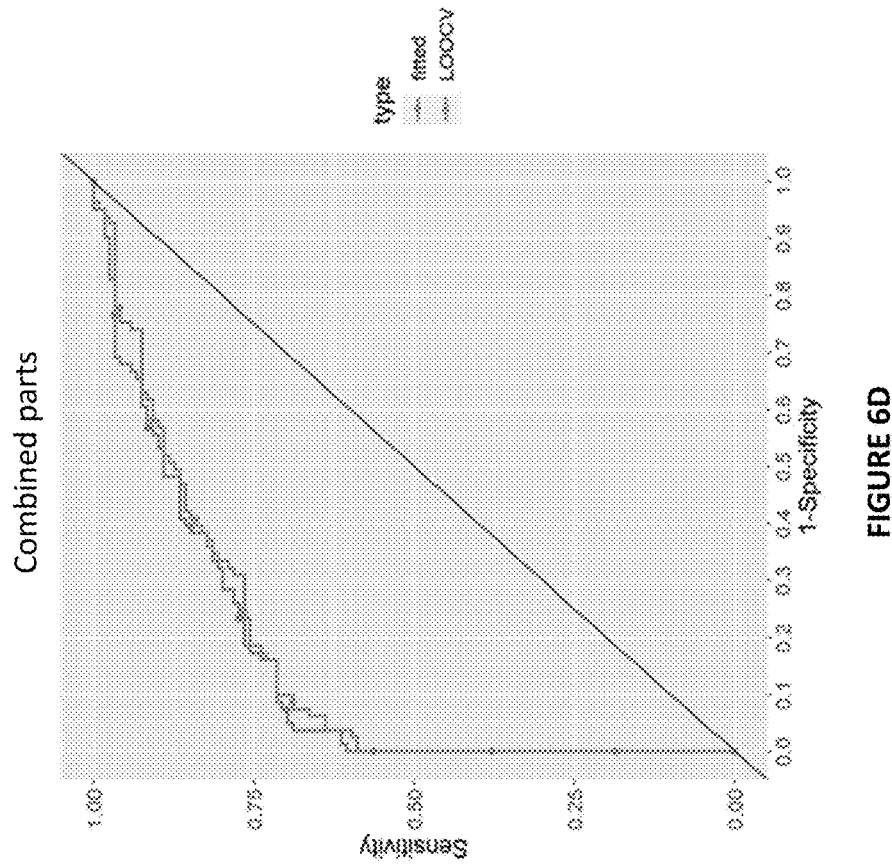
Figure 6C:
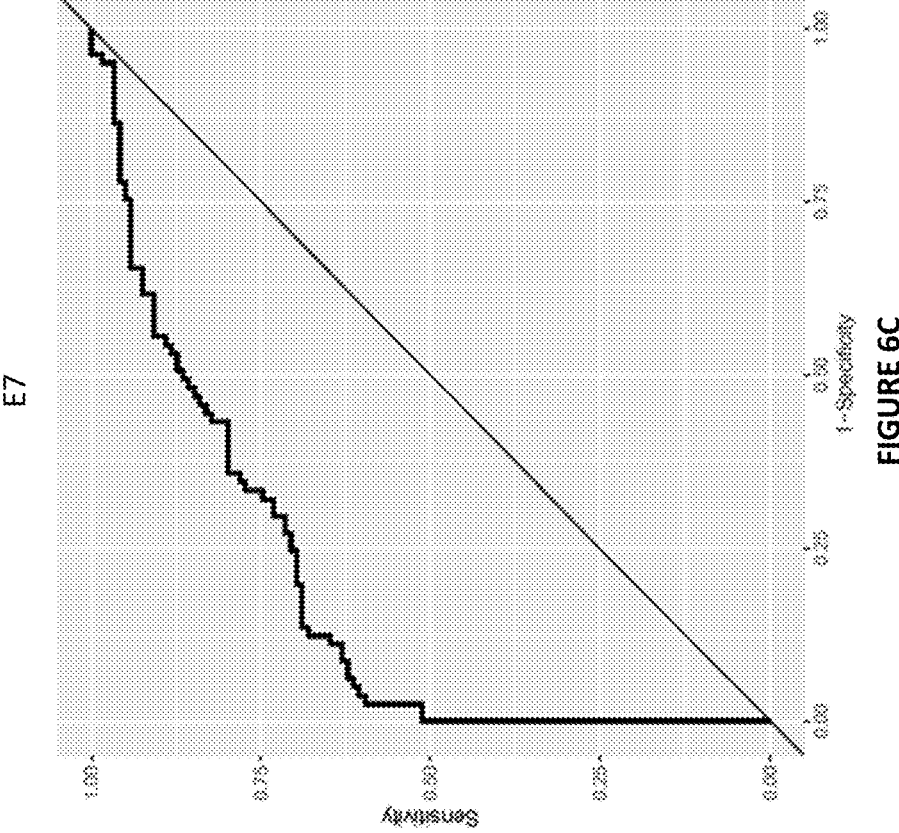

IgG Abs to three HPV16 antigens (CE2, NE6 and E7) were measured in baseline serum from 116 HPVOPC cases, 41 partners, and compared to 81 healthy volunteers (FIG. 5). The median of all HPV16 Abs in cases compared to volunteers (p<0.001) were increased. There was no significant difference observed between healthy volunteers and partners of HPVOPC cases for any HPV16 antibody except HPV16 NE6. Abs to E7 (68/119,57.1%) protein was common in cases follow by CE2 (57/119, 47.9%) and NE6 (38/119, 31.9%). Most HPVOPC cases had Abs to at least one early antigen (CE2, NE6, and/or E7)(91/119, 76.5%). The prevalence of serum IgG Abs among HPVOPC cases, and volunteers specific for HPV16 antigens is summarized in Table 1. This data was also compared with the data using RIPAD ELISA which we published previously (23). The sensitivity for each test was summarized in Table 2.

TABLE 1

| The prevalence of positive antibody response to each HPV16 protein. | | |
| --- | --- | --- |
| HPV16 antibodies | Case N = 119 | Control N = 81 |
| E6* | 38 (31.9%) | 3 (3.7%) |
| E2** | 57 (47.9%) | 4 (4.9%) |
| E7 | 68 (57.1%) | 1 (1.2%) |
| Any E | 91 (76.5%) | 6 (7.4%) |

*N-terminal fragment of E6.
**C-terminal fragment of E2. Cut-off values defined as signal to noise ration + 2 standard deviations for each antigen ins serum of controls.

TABLE 2

| The sensitivity and specificity of each assay. | | |
| --- | --- | --- |
| | HPV16 antibodies (Any E) | |
| | LFA | RAPID ELISA* |
| Sensitivity (n = 116) | 76.5% | 86.2% |
| Specificity (n = 81) | 92.6% | 97.5% |

Predictors of HPV16 Antibody Level

When examined individually, HPV16E6, HPV16E2, and HPV16E7 had significantly different plasma levels between HPVOPC and healthy controls. Based on the receiver operating characteristic (ROC) curves constructed and area under the curve (AUC) calculated, HPV17 E7 exhibited the greatest power to discriminate the case and control (AUC 0.83), followed by HPV16CE2 (AUC 0.77), and HPV16NE6 (AUC 0.71). At a fixed specificity of 90%, the sensitivity of discrimination of HPVOPC from healthy controls are 0.63 for HPV 16E7, 0.55 for HPV16 CE2 and 0.42 for HPV16 NE6. In addition, the AUC of ROC curve to the greatest extent when combining these three markers (AUC 0.85). Also, the sensitivity at a fixed specificity of 90% is increased to 0.71 when combing HPV16 CE2, NE6, and E7 (FIG. 6 and Table 3).

TABLE 3

| ROC performance of each biomarker. ROC Table | | | | | | | | | |
| --- | --- | --- | --- | --- | --- | --- | --- | --- | --- |
| | N = case | N = control | AUC | AUC 95% LL | AUC 95% UL | Normalized AUC On SP >= 0.9 | TH | OR | ST | SP |
| HPV16E7 | 119 | 81 | 0.83 | 0.77 | 0.88 | 0.59 | 1.73 | 15.55 | 0.63 | 0.9 |
| HPV16 CE2 | 119 | 81 | 0.77 | 0.70 | 0.83 | 0.45 | 1.95 | 10.98 | 0.55 | 0.9 |

TABLE 3-continued

| | | | | | | | | | |
|---|---|---|---|---|---|---|---|---|---|
| | | ROC performance of each biomarker. | | | | | | | |
| | | ROC Table | | | | | | | |
| | N = case | N = control | AUC | AUC 95% LL | AUC 95% UL | Normalized AUC On SP >= 0.9 | TH | OR | ST | SP |
| HPV16 NE6 | 119 | 81 | 0.71 | 0.64 | 0.78 | 0.35 | 1.41 | 6.61 | 0.42 | 0.9 |

AUC95% LL: lower confidence limit for the AUC; AUC95% UL: upper confidence limit for the AUC; TH; threshold value; OR: odds ration: ST: sensitivity; SP: specificity.

Potential Platform for Field Application

Next, we combined our assay with plasma separation membrane to evaluate its potential performance using whole blood for field application. There are significant technological impediments in the process of whole blood handling for biomarker detection. These challenges are aggravated in resource-limited settings. Most detection platforms require intensive sample preparation, centrifuges and additional resources that are not available in all fields. Here, we chose an inexpensive, rapid, easy-to-use and disposable filter based microfluidic plasma separator (Vivid GX plasma separation membrane) for the isolation of biomarkers as a sample preparation device. The Vivid GX plasma separation membrane (#NC1557225, Fisher Scientific) utilizes a highly asymmetric vertical membrane that filters out plasma from whole blood samples. The highly asymmetric membrane can capture the cellular components of the blood (red cells, white cells, and platelets) in the large pores and allow plasma to through the smaller pores on the downstream side of the membrane.

To evaluate the assay performance using whole blood to detect anti-EBNA-1 IgG. The EBNA-1 protein is highly immunogenic in 90% of healthy US blood donors. We assessed the functionality of the fully integrated device using purified viral EBNA-1 protein, a negative control (BSA), and positive control (IgG) proteins. During the evaluation process, different lengths of Vivid GX plasma separation membrane, incubation time of blood and EBNA-1, and washing condition were optimized (data not shown). Finally, we measured anti-EBNA-1 IgG from a finger prick of blood to attain intra- and inter-assay variability of <50%. According to the data, there was no more than a 2-fold difference of the variation in anti-EBNA-1 IgG detection between slides and printing batches that were analyzed and processed at different times for 20 healthy donors (FIG. 10B).

DISCUSSION

70% of oropharyngeal cancer cases in the United States are caused by Human papillomavirus (HPV), most notably HPV16 (24). Most assays for detection of HPVOPC are salivary diagnostic tests which involve the use of PCR/qPCR. These are lab-based tests that need an expensive machine and a well-trained operator (25-28). Besides, detection of HPV nucleic acid in samples provide high false negative rates since most HPV infections are self-cleared which may not be detectable (29-31). Therefore, antibody tests have high specificity compared to nucleic acid tests (25). Particularly, the serum antibodies against the HPV-16 E6, HPV16 E2, and HPV-16 E7 proteins are highly specific biomarkers for the presence of HPVOPC (25, 27, 32). There are some POC-based platforms developed to detect HPV antibody in plasma or blood. For example a device to detect and quantify anti-HPV E7 antibody was developed. However, the multiplexing capability was limited (33). Another study developed a luciferase-based detection (luciferase immunoprecipitation system) of HPV16 E2, E6, and E7 antibodies, but it takes 2.5 hours to finish the assay which might be prohibitive in some circumstances (26). Here, we developed not only a rapid, inexpensive, and user-friendly fluorescent serological lateral flow assay for HPVOPC, but also a multiplex format. It only needs less than 1 ul of plasma/serum to test three HPV antigens at the same time. This study demonstrates that our assay can detect 76.5% of HPVOPC patients that have generated an immunologic response against the virus for at least one HPV16 early protein. Antibodies to E7 ($^{57.1}$%) protein was common in cases followed by CE2 (47.9%) and NE6 (31.9%). Our results are inconsistent with other published literatures (27, 32, 34), as HPV16 E7 antigen was found to have a higher sensitivity than the E2 and E6 antigen (Tables 1 and 2). This is probably due to having only N-terminal of E6 and C-terminal of E2 immobilized on the membrane in our assay. This differs from the full length of E6 and E2 used in other assays. We anticipate that mixing C-terminal and N-terminal HPV16 E6 and E2 can result in proteins to enhance test performance and the sensitivity.

One more challenge for LFAs has always been reproducibility, especially for serological testing in plasma samples. Some reports have already indicated that it has been difficult to reach acceptable levels of sensitivity for certain antigens. The ability to retain immunological activity between batches is also crucial for the reproducibility (35, 36). In this paper, we addressed this challenge by investigating the reproducibility between two batches of strips. We did not see a 2-fold difference in the variation of anti-HPV IgG detection between slides across two batches (FIG. 8). Storage condition is another factor to affect the performance of strips. In order to investigate the effect of long-term storage at room temperature, the strips were sealed in different bags with desiccants using a vacuum sealer machine. Every month, we ran the experiments and compared the signals from previous month. From our data (FIG. 9), the signal of anti-HPV16 NE6 antibody, not HPV16 CE2 and HPV16 E7 from the strip, decreased 30% after 3 months of storage. The strips are stable for two months of storage at room temperature. In the future, we will investigate the effect of the storage conditions.

It is not a surprise that our assay is not as sensitivity as RAPID ELISA (Table 2). There are different reasons to explain this. The first reason is that the signal from the RAPID ELISA is amplified using chemiluminescence. The second reason is the incubation time of sample and antigen. There is one-hour incubation time in RAPID ELISA; however, only few seconds of interaction of sample and antigen in lateral flow assay. The third reason is that the full length of HPV16 E6 is applied in RAPID ELISA. However, only N-terminal of HPV16 E6 is utilized in lateral flow assay. These reasons increase the sensitivity of RAPID ELISA.

To date there are no commercial assays for HPV testing approved by FDA for head and neck cancer, but there are products to test cervical cancer. For example, the OncoE6TM Oral test from Arbor Vita is a lateral flow test device used to detect the presence of E6 proteins from HPV16 and HPV18. However, the test usually takes 2.5 hours which is long for a POC test. Second, Cobas HPV PCR testing from Roche identifies genotypes 16 and 18, and other 12 high-risk HPV genotypes as well. However, this test is limited to use the Cobasx480 instrument and the Cobas z 480 analyzers. No other sample preparation instrument or PCR system can be compatible with this test. Furthermore, DNA testing cannot discriminate between transient and persistent HPV infections since most HPV infections are transient and the immune system usually eliminates the virus in 12-36 months (37, 38). A third example is the Aptima HPV testing from Hologic that measures E6/E7 mRNA of 14 high-risk HPV genotypes using real-time amplification. This system can run up to 250 tests in about five hours in a laboratory setting environment; this cannot be considered a point of care testing and is difficult to reproduce on a clinical site(39). In this study, our assay/device overcomes the overall limitations of other commercially available products including cost of materials, equipment, time, and well-trained operators, making it a true point-of-care system. In conclusion, we demonstrated that our assay is a rapid, inexpensive, and user-friendly test for diagnosing and identifying HPVOPC patients, especially in limited resource environments.

Materials and Methods

Sera Sample Collections

The sera from 119 cases, 41 partners, and 81 healthy volunteers were from the HOTSPOT (Human Oral Papillomavirus Transmission in Partners over Time) study which has been previously reported (10, 23).

Fluorescent Microsphere Conjugation

Carboxyl-modified fluorescent FlY050 microspheres were conjugated to Goat anti-human IgG (#109-005-008, Jackson ImmunoResearch Laboratories) using a two-step EDC (#22980, Thermo Scientific)/Sulfo-NHS (#24510, Thermo Scientific) covalent coupling procedure. The details of this process have been detailed previously by Millipore (40).

Expression and Purification of HPV16 Protein

N-terminal of HPV16 E6(1-86), C-terminal of HPV16 E6 (70-100) and HPV (87-158), C-terminal of HPV16 E2 (184-365), and full length HPV16 E7 gene were transferred into the Gateway compatible destination vector pDEST15 from pDONR221. Expression vectors were transformed into *E. coli* strain BL21DE3 and isolated colonies were grown in Luria broth (LB) media for overnight at 37° C. The cultures were grown in LB media at 37° C. until OD600 of 0.6-0.7 was reached and followed by induction with 1 mM isopropyl P-D-1-thiogalactopyranoside (IPTG) (#I6758-10G, Sigma-Aldrich) for 19 hours at 22° C. After 19 hours of incubation, the cells were centrifuged at 5000×g for 20 min at 4° C., re-suspended pellets in lysis buffer (KH2PO4/K2HPO4/NaCl/KCl pH7.8, 1× FastBreak cell lysis reagent, 4 mg/mL Lysozyme, 1 mM DTT, 25 µg/ml Deoxy ribonuclease (DNase), 5 mM MgSO4, 100 µM Phenyl methyl sulfonyl fluoride(PMSF)). Flash freeze lysis buffer using dry ice and ethanol until completely frozen and thaw it completely in 37° C. water bath. Repeat this step for another three times. After four times, the lysate was centrifuged at 5000×g for 20 min at 4° C. and the supernatant was mixed with glutathione sepharose resins (#95017-174, VWR) for overnight at 4° C. The resins were washed five times with washing buffer (50 mM NaCl, 50 mM Tris, 1 mM DTT, and 1 mM EDTA). Protein was eluted with elution buffer (50 mM Tris, 10 mM reduced Glutathione, pH 8). Bradford assay was used to quantitate the protein using bovine serum albumin (BSA) protein standard. Purity of HPV16 proteins were determined by Sodium dodecyl Sulfate (SDS) poly acrylamide gel electrophoresis (PAGE) (FIG. 1).

Evaluation of Recombinant Proteins by ELISA 96-well plates were coated overnight at 4° C. with the recombinant proteins (20 ng/well for HPV16 E7 and HPV 16CE2, 40 ng/well for HPV 16 E6). Plates were subsequently washed 5 times with PBS (BP6651, Fisher Scientific) 0.2% Tween 20 (#P1379-1L, Sigma-Aldrich) (PBS-T) and blocked with 200 µl of 5% (wt/vol) skimmed milk (0290288725, MP Biomedicals) in PBST (0.2%) for 1 h at room temperature. The wells were washed 5 times with PBST (0.2%) and incubated with 100 µl of different dilutions of sera that was already blocked with *Escherichia coli* lysate and 0.2% milk-PBST for overnight. After 1 hour of incubation with sera, plates were then washed 5 times with PBST (0.2%) and incubated with anti-human IgG antibodies (Jackson ImmunoResearch Laboratories, West Grove, PA) at 1:10,000 for 1 hour. The wells were washed 5 times with PBST (0.2%) after 1 hour and detected the signals using Supersignal ELISA Femto chemiluminescent substrate (#37074, Thermo Scientific). Luminescence was detected as relative light units (RLU) on a Glomax 96 microplate luminometer (Promega, Madison, WI) at 425 nm. The ratio of RLU for individual HPV-specific antibodies to RLU for the control GST-antigen was measured.

Assembly of Lateral Flow Assay

BSA (25 mg/ML), HPV 16NE6 (1 mg/mL), HPV16 CE2 (0.5 mg/mL), HPV16 E7 (0.5 mg/mL) and human IgG (0.4 mg/mL) proteins were dispensed on test lines and a control line of a nitrocellulose membrane using a dispenser (XYZ3060™, Biodot). Nitrocellulose membrane sheets (#1UN95ER100050NT, Sartorius) and the absorbent pads were assembled and then were cut into 50 mm×5 mm strips by a cutter (Matrix 2360, Kinematic Automation) and mounted on glass slides (#16004-422, VWR) with adhesive (#GBL620001-1EA, Sigma-Aldrich). The slides were in the desiccator for overnight before doing the lateral flow assay.

Anti-HPV16 IgG Lateral Flow Assay

Plasma samples were diluted (1:50) in PBS solution. Add 50 mL of PBST(0.2%) to pre-wet the strip. A 30 mL sample of diluted plasma was added upstream of the strip and allowed to flow through the strip by capillary action for 15 minutes. After 15 minutes, the strips were washed by flowing 100 mL of PBST through the test strip in two steps of 50 mL each aliquot. Then 60 mL of diluted anti-human IgG conjugated with FlY050 microspheres (#FR180380534, EMD Milipore) (5.74×107 estimated number of microspheres based on initial concentration) suspended in Block-Aid (#B10710, Life Technologies)/PBST were applied to the strips in two steps of 30 mL each aliquot and allowed to flow through for 20 minutes. The strips were washed with 100 mL of PBST in two steps of 50 mL each aliquot. After the washing steps, the strips were dried on a hot plate at 37° C. for 10 minutes. The results were assessed by detection in our point of care fluorescent reader (41).

Finger-Stick Platform

EBNA-1 (test line), BSA (negative control), and IgG (positive control) were dispensed on three sites spaced at 6 mm intervals on the same nitrocellulose. 7 mm of Vivid GX plasma separation membrane was attached the sample pad (9 mm) followed by the nitrocellulose (40 mm) and the absorbent pad (27 mm). A 60 mL of PBST (0.2%) was added to the LFA strip for pre-wet step. 5 μl of normal donor whole blood was added to plasma separation membrane, chased with 60 μl running buffer for 25 mins incubation, and strips were washed with 100 mL of PBST in two steps of 50 mL each aliquot. Then 60 mL of diluted anti-human IgG conjugated with FIY050 microspheres (5.74×107 estimated number of microspheres based on initial concentration) suspended in BlockAid/PBST were applied to the strips in two steps of 30 mL each aliquot and allowed to flow through for 20 minutes. After 20 minutes, the strips were washed by flowing 100 μL of PBST through the test strip in two steps of 50 μL each aliquot. The strips were washed with 100 μL of PBST in two steps of 50 μL each aliquot. After the washing steps, the strips were dried on a hot plate at 37° C. for 10 minutes. The results were assessed by detection in a point of care fluorescent reader (41).

Data Analysis

Our fluorescent reader was built in house which was described previously (41) and it detects the fluorescent signal from the control line and test line as a photocurrent. The system then converts and denoises the signal using a charge integration readout which converts the generated current to a voltage output (41). In our experiments, we interpreted the signal by measuring the time required for the reading circuit to reach a voltage threshold of 4.88 V. Thus, a smaller time difference correlates with a higher fluorescent signal. The test line intensity was normalized to the negative control site (Signal to Noise).

As described herein, the disclosed compositions, assays, systems, and devices overcome the overall limitations of other commercially available products including cost of materials, equipment, time, and well-trained operators, making it a true point-of-care system. In conclusion, we demonstrated that our assay is a rapid, inexpensive, and user-friendly test for diagnosing and identifying HPV positive patients using blood, serum, plasma, and human biofluid samples, for example saliva, especially in limited resource environments.

REFERENCES

1. Chow L Q M. Head and Neck Cancer. N Engl J Med. 2020; 382(1):60-72. Epub 2020/01/02. doi: 10.1056/ NEJMra1715715. PubMed PMID: 31893516.
2. Siegel R L, Miller K D, Jemal A. Cancer statistics, 2020. CA Cancer J Clin. 2020; 70(1):7-30. Epub 2020/01/09. doi: 10.3322/caac.21590. PubMed PMID: 31912902.
3. Morbini P, Benazzo M. Human papillomavirus and head and neck carcinomas: focus on evidence in the babel of published data. Acta Otorhinolaryngol Ital. 2016; 36(4): 249-58. Epub 2016/10/14. doi: 10.14639/0392-100X-853. PubMed PMID: 27734976; PMCID: PMC5066459.
4. Thomas G R, Jefferson G. Chapter 64—Head and Neck Cancer. In: Ginsburg G S, Willard H F, editors. Genomic and Personalized Medicine (Second Edition): Academic Press; 2013. p. 742-8.
5. Kreimer A R, Clifford G M, Boyle P, Franceschi S. Human papillomavirus types in head and neck squamous cell carcinomas worldwide: a systematic review. Cancer Epidemiol Biomarkers Prev. 2005; 14(2):467-75. Epub 2005/ 03/01. doi: 10.1158/1055-9965.EPI-04-0551. PubMed PMID: 15734974.
6. Chen Z W, Weinreb I, Kamel-Reid S, Perez-Ordonez B. Equivocal p16 immunostaining in squamous cell carcinoma of the head and neck: staining patterns are suggestive of HPV status. Head Neck Pathol. 2012; 6(4):422-9. Epub 2012/07/18. doi: 10.1007/s12105-012-0382-3. PubMed PMID: 22801997; PMCID: PMC3500888.
7. Guo W Z F M Q S. Gynecologic and Obstetric Pathology, Volume 2: Springer, Singapore; 2019.
8. Kim K Y, Lewis J S, Jr., Chen Z. Current status of clinical testing for human papillomavirus in oropharyngeal squamous cell carcinoma. J Pathol Clin Res. 2018; 4(4):213-26. Epub 2018/07/31. doi: 10.1002/cjp2.111. PubMed PMID: 30058293; PMCID: PMC6174616.
9. Pierce Campbell C M, Kreimer A R, Lin H Y, Fulp W, O'Keefe M T, Ingles D J, Abrahamsen M, Villa L L, Lazcano-Ponce E, Giuliano A R. Long-term persistence of oral human papillomavirus type 16: the HPV Infection in Men (HIM) study. Cancer Prev Res (Phila). 2015; 8(3): 190-6. Epub 2015/01/13. doi: 10.1158/1940-6207.CAPR-14-0296. PubMed PMID: 25575501; PMCID: PMC4355174.
10. D'Souza G, Gross N D, Pai S I, Haddad R, Anderson K S, Rajan S, Gerber J, Gillison M L, Posner M R. Oral human papillomavirus (HPV) infection in HPV-positive patients with oropharyngeal cancer and their partners. J Clin Oncol. 2014; 32(23):2408-15. Epub 2014/04/30. doi: 10.1200/JCO.2014.55.1341. PubMed PMID: 24778397; PMCID: PMC4263818.
11. Evander M, Edlund K, Gustafsson A, Jonsson M, Karlsson R, Rylander E, Wadell G. Human papillomavirus infection is transient in young women: a population-based cohort study. J Infect Dis. 1995; 171(4):1026-30. Epub 1995/04/01. doi: 10.1093/infdis/171.4.1026. PubMed PMID: 7706782.
12. Hsing A W, Schiffman M, Zhang T, Greer C E, Chen C J, You S L, Hsieh C Y, Huang T W, Liaw K L, Manos M. Persistence of type-specific human papillomavirus infection among cytologically normal women. J Infect Dis. 1994; 170(2):498. Epub 1994/08/01. doi: 10.1093/infdis/ 170.2.498. PubMed PMID: 8035046.
13. Marur S, D'Souza G, Westra W H, Forastiere A A. HPV-associated head and neck cancer: a virus-related cancer epidemic. Lancet Oncol. 2010; 11(8):781-9. Epub 2010/05/11. doi: 10.1016/S1470-2045(10)70017-6. PubMed PMID: 20451455; PMCID: PMC5242182.
14. Dahlstrom K R, Anderson K S, Field M S, Chowell D, Ning J, Li N, Wei Q, Li G, Sturgis E M. Diagnostic accuracy of serum antibodies to human papillomavirus type 16 early antigens in the detection of human papillomavirus-related oropharyngeal cancer. Cancer. 2017; 123(24):4886-94. Epub 2017/09/13. doi: 10.1002/ cncr.30955. PubMed PMID: 28898394; PMCID: PMC5716885.
15. Silverberg M J, Schneider M F, Silver B, Anastos K M, Burk R D, Minkoff H, Palefsky J, Levine A M, Viscidi R P. Serological detection of human papillomavirus type 16 infection in human immunodeficiency virus (HIV)-positive and high-risk HIV-negative women. Clin Vaccine Immunol. 2006; 13(4):511-9. Epub 2006/04/11. doi: 10.1128/CVI.13.4.511-519.2006. PubMed PMID: 16603621; PMCID: PMC1459636.
16. Fakhry C, Qualliotine J R, Zhang Z, Agrawal N, Gaykalova D A, Bishop J A, Subramaniam R M, Koch W M, Chung C H, Eisele D W, Califano J, Viscidi R P. Serum Antibodies to HPV16 Early Proteins Warrant Investigation as Potential Biomarkers for Risk Stratification and Recurrence of HPV-Associated Oropharyngeal Cancer. Cancer Prev Res (Phila). 2016; 9(2):135-41. Epub 2015/ 12/25. doi: 10.1158/1940-6207.CAPR-15-0299. PubMed PMID: 26701665; PMCID: PMC4811031.

17. Spector M E, Sacco A G, Bellile E, Taylor J M G, Jones T, Sun K, Brown W C, Birkeland A C, Bradford C R, Wolf G T, Prince M E, Moyer J S, Malloy K, Swiecicki P, Eisbruch A, McHugh J B, Chepeha D B, Rozek L, Worden F P. E6 and E7 Antibody Levels Are Potential Biomarkers of Recurrence in Patients with Advanced-Stage Human Papillomavirus-Positive Oropharyngeal Squamous Cell Carcinoma. Clin Cancer Res. 2017; 23(11):2723-9. Epub 2016/11/23. doi: 10.1158/1078-0432.CCR-16-1617. PubMed PMID: 27872102; PMCID: PMC5438906.

18. Katchman B A, Smith J T, Obahiagbon U, Kesiraju S, Lee Y K, O'Brien B, Kaftanoglu K, Blain Christen J, Anderson K S. Application of flat panel OLED display technology for the point-of-care detection of circulating cancer biomarkers. Sci Rep. 2016; 6:29057. Epub 2016/07/05. doi: 10.1038/srep29057. PubMed PMID: 27374875; PMCID: PMC4931450.

19. Verma R R, Sriraman R, Rana S K, Ponnanna N M, Rajendar B, Ghantasala P, Rajendra L, Matur R V, Srinivasan V A. E6 protein of human papillomavirus 16 (HPV16) expressed in *Escherichia coli* sans a stretch of hydrophobic amino acids, enables purification of GST-DeltaE6 in the soluble form and retains the binding ability to p53. Protein Expr Purif 2013; 92(1):41-7. Epub 2013/09/10. doi: 10.1016/j.pep.2013.08.010. PubMed PMID: 24012792.

20. Illiano E, Demurtas O C, Massa S, Di Bonito P, Consalvi V, Chiaraluce R, Zanotto C, De Giuli Morghen C, Radaelli A, Venuti A, Franconi R. Production of functional, stable, unmutated recombinant human papillomavirus E6 oncoprotein: implications for HPV-tumor diagnosis and therapy. J Transl Med. 2016; 14(1):224. Epub 2016/07/29. doi: 10.1186/s12967-016-0978-6. PubMed PMID: 27465494; PMCID: PMC4963926.

21. Xu W X, Wang J, Tang H P, He Y P, Zhu Q X, Gupta S K, Gu S H, Huang Q, Ji C N, Liu L F, Li G L, Xu C J, Xie Y. Epitomics: IgG-epitome decoding of E6, E7 and L1 proteins from oncogenic human papillomavirus type 58. Sci Rep. 2016; 6:34686. Epub 2016/10/07. doi: 10.1038/srep34686. PubMed PMID: 27708433; PMCID: PMC5052575.

22. Hou C, Zhu M, Anderson K S, Obahiagbon U, Christen J B, editors. Assay Development and Storage for Fluorescence-Based Lateral Flow Immunoassay. 2018 IEEE Life Sciences Conference (LSC); 2018 28-30 Oct. 2018.

23. Anderson K S, Gerber J E, D'Souza G, Pai S I, Cheng J N, Alam R, Kesiraju S, Chowell D, Gross N D, Haddad R, Gillison M L, Posner M. Biologic predictors of serologic responses to HPV in oropharyngeal cancer: The HOTSPOT study. Oral Oncol. 2015; 51(8):751-8. Epub 2015/06/23. doi: 10.1016/j.oraloncology.2015.05.007. PubMed PMID: 26094591; PMCID: PMC4982366.

24. Chaturvedi A K, Engels E A, Pfeiffer R M, Hernandez B Y, Xiao W, Kim E, Jiang B, Goodman M T, Sibug-Saber M, Cozen W, Liu L, Lynch C F, Wentzensen N, Jordan R C, Altekruse S, Anderson W F, Rosenberg P S, Gillison M L. Human papillomavirus and rising oropharyngeal cancer incidence in the United States. J Clin Oncol. 2011; 29(32):4294-301. Epub 2011/10/05. doi: 10.1200/JCO.2011.36.4596. PubMed PMID: 21969503; PMCID: PMC3221528.

25. D'Souza G, Clemens G, Troy T, Castillo R G, Struijk L, Waterboer T, Bender N, Pierorazio P M, Best S R, Strickler H, Wiley D J, Haddad R I, Posner M, Fakhry C. Evaluating the Utility and Prevalence of HPV Biomarkers in Oral Rinses and Serology for HPV-related Oropharyn-geal Cancer. Cancer Prev Res (Phila). 2019; 12(10):689-700. Epub 2019/08/20. doi: 10.1158/1940-6207.CAPR-19-0185. PubMed PMID: 31420362; PMCID: PMC7029397.

26. Burbelo P D, Chaturvedi A, Notkins A L, Gunti S. Luciferase-Based Detection of Antibodies for the Diagnosis of HPV-Associated Head and Neck Squamous Cell Carcinoma. Diagnostics (Basel). 2019; 9(3). Epub 2019/08/09. doi: 10.3390/diagnostics9030089. PubMed PMID: 31390810; PMCID: PMC6787723.

27. Kreimer A R, Johansson M, Waterboer T, Kaaks R, Chang-Claude J, Drogen D, Tjonneland A, Overvad K, Quiros J R, Gonzalez C A, Sanchez M J, Larranaga N, Navarro C, Barricarte A, Travis R C, Khaw K T, Wareham N, Trichopoulou A, Lagiou P, Trichopoulos D, Peeters P H, Panico S, Masala G, Grioni S, Tumino R, Vineis P, Bueno-de-Mesquita H B, Laurell G, Hallmans G, Manjer J, Ekstrom J, Skeie G, Lund E, Weiderpass E, Ferrari P, Byrnes G, Romieu I, Riboli E, Hildesheim A, Boeing H, Pawlita M, Brennan P. Evaluation of human papillomavirus antibodies and risk of subsequent head and neck cancer. J Clin Oncol. 2013; 31(21):2708-15. Epub 2013/06/19. doi: 10.1200/JCO.2012.47.2738. PubMed PMID: 23775966; PMCID: PMC3709056.

28. Tang K D, Vasani S, Taheri T, Walsh L J, Hughes B G M, Kenny L, Punyadeera C. An Occult HPV-Driven Oropharyngeal Squamous Cell Carcinoma Discovered Through a Saliva Test. Front Oncol. 2020; 10:408. Epub 2020/04/17. doi: 10.3389/fonc.2020.00408. PubMed PMID: 32296641; PMCID: PMC7136454.

29. Corstjens P L, Abrams W R, Malamud D. Detecting viruses by using salivary diagnostics. J Am Dent Assoc. 2012; 143(10 Suppl):12S-8S. Epub 2012/10/17. doi: 10.14219/jada.archive.2012.0338. PubMed PMID: 23034833; PMCID: PMC4262792.

30. Won K H, Lee J Y, Cho H Y, Suh D H, No J H, Kim Y B. Impact of age on the false negative rate of human papillomavirus DNA test in patients with atypical squamous cells of undetermined significance. Obstet Gynecol Sci. 2015; 58(2):117-23. Epub 2015/03/24. doi: 10.5468/ogs.2015.58.2.117. PubMed PMID: 25798425; PMCID: PMC4366864.

31. Kubik M J, Permenter T, Saremian J. Specimen Age Stability for Human Papilloma Virus DNA Testing Using BD SurePath. Lab Med. 2015; 46(1):51-4; quiz e13. Epub 2015/01/27. doi: 10.1309/LM87NED5LRSELUOQ. PubMed PMID: 25617393.

32. Kreimer A R, Ferreiro-Iglesias A, Nygard M, Bender N, Schroeder L, Hildesheim A, Robbins H A, Pawlita M, Langseth H, Schlecht N F, Tinker L F, Agalliu I, Smoller S W, Ness-Jensen E, Hveem K, D'Souza G, Visvanathan K, May B, Ursin G, Weiderpass E, Giles G G, Milne R L, Cai Q, Blot W J, Zheng W, Weinstein S J, Albanes D, Brenner N, Hoffman-Bolton J, Kaaks R, Barricarte A, Tjonneland A, Sacerdote C, Trichopoulou A, Vermeulen R C H, Huang W Y, Freedman N D, Brennan P, Waterboer T, Johansson M. Timing of HPV16-E6 antibody seroconversion before OPSCC: findings from the HPVC3 consortium. Ann Oncol. 2019; 30(8):1335-43. Epub 2019/06/12. doi: 10.1093/annonc/mdzl38. PubMed PMID: 31185496; PMCID: PMC6683856.

33. Inan H, Wang S, Inci F, Baday M, Zangar R, Kesiraju S, Anderson K S, Cunningham B T, Demirci U. Isolation, Detection, and Quantification of Cancer Biomarkers in HPV-Associated Malignancies. Sci Rep. 2017; 7(1):3322. Epub 2017/06/14. doi: 10.1038/s41598-017-02672-6. PubMed PMID: 28607383; PMCID: PMC5468352.

34. Holzinger D, Wichmann G, Baboci L, Michel A, Hofler D, Wiesenfarth M, Schroeder L, Boscolo-Rizzo P, Herold-Mende C, Dyckhoff G, Boehm A, Del Mistro A, Bosch F X, Dietz A, Pawlita M, Waterboer T. Sensitivity and specificity of antibodies against HPV16 E6 and other early proteins for the detection of HPV16-driven oropharyngeal squamous cell carcinoma. Int J Cancer. 2017; 140(12):2748-57. Epub 2017/03/21. doi: 10.1002/ijc.30697. PubMed PMID: 28316084.

35. Baumann R, Kaempfer S, Chegou N N, Oehlmann W, Loxton A G, Kaufmann S H, van Helden P D, Black G F, Singh M, Walzl G. Serologic diagnosis of tuberculosis by combining Ig classes against selected mycobacterial targets. J Infect. 2014; 69(6):581-9. Epub 2014/06/27. doi: 10.1016/j.jinf2014.05.014. PubMed PMID: 24968240.

36. Ellington A A, Kullo I J, Bailey K R, Klee G G. Antibody-based protein multiplex platforms: technical and operational challenges. Clin Chem. 2010; 56(2):186-93. Epub 2009/12/05. doi: 10.1373/clinchem.2009.127514. PubMed PMID: 19959625; PMCID: PMC2901849.

37. Moscicki A B, Palefsky J, Smith G, Siboshski S, Schoolnik G. Variability of human papillomavirus DNA testing in a longitudinal cohort of young women. Obstet Gynecol. 1993; 82(4 Pt 1):578-85. Epub 1993/10/01. PubMed PMID: 8397358.

38. Wu M Z, Li W N, Cha N, Tian L X, Zhang Y I, Wu X, Guo K J, Wu G P. Diagnostic Utility of HPV16 E6 mRNA or E7 mRNA Quantitative Expression for Cervical Cells of Patients with Dysplasia and Carcinoma. Cell Transplant. 2018; 27(9):1401-6. Epub 2018/07/31. doi: 10.1177/0963689718788521. PubMed PMID: 30056761; PMCID: PMC6168995.

39. Taberna M, Mena M, Pavon M A, Alemany L, Gillison M L, Mesia R. Human papillomavirus-related oropharyngeal cancer. Ann Oncol. 2017; 28(10):2386-98. Epub 2017/06/22. doi: 10.1093/annonc/mdx304. PubMed PMID: 28633362.

40. Millipore M. Microsphere Coupling—Two-step EDC/Sulfo NHS Covalent Coupling Procedure for Estapor Carboxyl-modified Dyed Microspheres 2015.

41. Obahiagbon U, Smith J T, Zhu M, Katchman B A, Arafa H, Anderson K S, Blain Christen J M. A compact, low-cost, quantitative and multiplexed fluorescence detection platform for point-of-care applications. Biosens Bioelectron. 2018; 117:153-60. Epub 2018/06/13. doi: 10.1016/j.bios.2018.04.002. PubMed PMID: 29894852; PMCID: PMC6095205.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

---

SEQUENCE LISTING

```
Sequence total quantity: 4
SEQ ID NO: 1              moltype = AA   length = 158
FEATURE                   Location/Qualifiers
source                    1..158
                          mol_type = protein
                          organism = unidentified
SEQUENCE: 1
MHQKRTAMFQ DPQERPRKLP QLCTELQTTI HDIILECVYC KQQLLRREVY DFAFRDLCIV   60
YRDGNPYAVC DKCLKFYSKI SEYRHYCYSL YGTTLEQQYN KPLCDLLIRC INCQKPLCPE  120
EKQRHLDKKQ RFHNIRGRWT GRCMSCCRSS RTRRETQL                          158

SEQ ID NO: 2              moltype = AA   length = 98
FEATURE                   Location/Qualifiers
source                    1..98
                          mol_type = protein
                          organism = unidentified
SEQUENCE: 2
MHGDTPTLHE YMLDLQPETT DLYCYEQLND SSEEDEIDG PAGQAEPDRA HYNIVTFCCK    60
CDSTLRLCVQ STHVDIRTLE DLLMGTLGIV CPICSQKP                           98

SEQ ID NO: 3              moltype = AA   length = 365
FEATURE                   Location/Qualifiers
source                    1..365
                          mol_type = protein
                          organism = unidentified
SEQUENCE: 3
METLCQRLNV CQDKILTHYE NDSTDLRDHI DYWKHMRLEC AIYYKAREMG FKHINHQVVP    60
TLAVSKNKAL QAIELQLTLE TIYNSQYSNE KWTLQDVSLE VYLTAPTGCI KKHGYTEVQ   120
FDGDICNTMH YTNWTHIYIC EEASVTVVEG QVDYYGLYYV HEGIRTYFVQ FKDDAEKYSK  180
NKVWEVHAGG QVILCPTSVF SSNEVSSPEI IRQHLANHPA ATHTKAVALG TEETQTTIQR  240
```

US 12,584,918 B2

-continued

```
PRSEPDTGNP CHTTKLLHRD SVDSAPILTA FNSSHKGRIN CNSNTTPIVH LKGDANTLKC  300
LRYRFKKHCT LYTAVSSTWH WTGHNVKHKS AIVTLTYDSE WQRDQFLSQV KIPKTITVST  360
GFMSI                                                             365

SEQ ID NO: 4            moltype = AA   length = 182
FEATURE                 Location/Qualifiers
source                  1..182
                        mol_type = protein
                        organism = unidentified
SEQUENCE: 4
WEVHAGGQVI LCPTSVFSSN EVSSPEIIRQ HLANHPAATH TKAVALGTEE TQTTIQRPRS  60
EPDTGNPCHT TKLLHRDSVD SAPILTAFNS SHKGRINCNS NTTPIVHLKG DANTLKCLRY  120
RFKKHCTLYT AVSSTWHWTG HNVKHKSAIV TLTYDSEWQR DQFLSQVKIP KTITVSTGFM  180
SI                                                                182
```

We claim:

1. A composition comprising (a), (b), and (c), linked to a solid support:
   (a) human papillomavirus type 16 (HPV16) E6 variant polypeptides, wherein the variant polypeptides consist of:
      (i) a variant of SEQ ID NO: 1 having a deletion of amino acids 30-35 of SEQ ID NO: 1 (HPV16 E6 (Del30-35)),
      (ii) a fragment of SEQ ID NO: 1 consisting of amino acids 70-100 of SEQ ID NO: 1 HPV16 E6 (70-100)),
      (iii) a fragment of SEQ ID NO: 1 consisting of amino acids 87-158 of SEQ ID NO: 1 (HPV16 E6 (87-158)), and
      (iv) a fragment of SEQ ID NO: 1 consisting of amino acids 1-86 of SEQ ID NO: 1 ((HPV16 E6 (1-86)),
   (b) HPV16 E2 polypeptide consisting of SEQ ID NO: 4, and
   (c) HPV E7 polypeptide (SEQ ID NO: 2).

2. A nucleic acid molecule, wherein the nucleic acid molecule comprises one or more sequences encoding human papillomavirus type 16 (HPV16) E6 or E2 variant polypeptides, wherein the variant polypeptides consist of:
   (a) a variant of SEQ ID NO: 1 having a deletion of amino acids 30-35 (HPV16 E6 (Del30-35)) of SEQ ID NO: 1;
   (b) a fragment of SEQ ID NO: 1 consisting of amino acids 70-100 of SEQ ID NO: 1 (HPV16 E6 (70-100));
   (c) a fragment of SEQ ID NO: 1 consisting of amino acids 87-158 of SEQ ID NO: 1 (HPV16 E6 (87-158));
   (d) a fragment of SEQ ID NO: 1 consisting of amino acids 1-86 of SEQ ID NO: 1 ((HPV16 E6 (1-86));
   (e) SEQ ID NO: 4.

3. A vector comprising the nucleic acid molecule of claim 2.

4. An isolated cell comprising the vector of claim 3.

5. The cell of claim 4, wherein the cell is a prokaryotic cell or a eukaryotic cell.

6. The cell of claim 4, wherein the cell is a bacterial cell.

7. The cell of claim 4, wherein the cell is an *E. coli* cell.

8. The cell of claim 4, wherein the cell is selected from a yeast cell, an insect cell, a plant cell, or a mammalian cell.

9. The cell of claim 4, wherein the cell expresses the encoded polypeptide.

10. A method for detecting HPV antibodies, the method comprising:
   (a) contacting an antibody-containing sample from a subject to (i), (ii), and (iii):
      (i) human papillomavirus type 16 (HPV16) E6 variant polypeptides, wherein the variant polypeptides consist of:
         (A) a variant of SEQ ID NO: 1 having a deletion of amino acids 30-35 (HPV16 E6 (Del30-35)) of SEQ ID NO: 1,
         (B) a fragment of SEQ ID NO: 1 consisting of amino acids 70-100 of SEQ ID NO: 1 (HPV16 E6 (70-100)),
         (C) a fragment of SEQ ID NO: 1 consisting of amino acids 87-158 of SEQ ID NO: 1 (HPV16 E6 (87-158)), and
         (D) a fragment of SEQ ID NO: 1 consisting of amino acids 1-86 of SEQ ID NO: 1 ((HPV16 E6 (1-86)):
      (ii) HPV16 E2 polypeptide consisting of SEQ ID NO: 4; and
      (iii) HPV E7 polypeptide (SEQ ID NO: 2);
      to form a binding reaction;
   (b) incubating the binding reaction under conditions to allow antibody to bind the HPV16 polypeptides and form a polypeptide-antibody complex;
   (c) detecting the complex.

11. The method of claim 10, wherein detecting the complex comprises contacting the complex with a detection reagent, wherein the detection reagent comprises a detectable label, and wherein the detection reagent binds the complex.

12. The method of claim 11, wherein the detectable label comprises a fluorescent label.

13. The method of claim 11, wherein the detection reagent comprises an antibody.

14. The method of claim 10, wherein elements (i)-(iii) of step (a) are linked to a solid support.

15. The method of claim 10, wherein the subject sample is selected from blood, serum, plasma, sputum, lymph, and cerebrospinal fluid.

* * * * *